United States Patent
Baley et al.

(10) Patent No.: US 10,138,526 B2
(45) Date of Patent: Nov. 27, 2018

(54) MOLECULAR MARKERS ASSOCIATED WITH STEM CANKER RESISTANCE IN SOYBEAN

(75) Inventors: George J. Baley, St. Louis, MO (US); Vergel C. Concibido, St. Louis, MO (US); Ryan Rapp, St. Louis, MO (US); Dennis Yang, St. Louis, MO (US); Jennifer J. Yates, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 1278 days.

(21) Appl. No.: 14/241,291

(22) PCT Filed: Aug. 29, 2012

(86) PCT No.: PCT/US2012/052766
§ 371 (c)(1),
(2), (4) Date: Jul. 1, 2014

(87) PCT Pub. No.: WO2013/033143
PCT Pub. Date: Mar. 7, 2013

(65) Prior Publication Data
US 2014/0310833 A1 Oct. 16, 2014

Related U.S. Application Data

(60) Provisional application No. 61/529,889, filed on Aug. 31, 2011.

(51) Int. Cl.
C12Q 1/68 (2018.01)
C12Q 1/6895 (2018.01)
A01H 1/04 (2006.01)
A01H 5/10 (2018.01)

(52) U.S. Cl.
CPC ............ *C12Q 1/6895* (2013.01); *A01H 1/04* (2013.01); *A01H 5/10* (2013.01); *C12Q 2600/172* (2013.01)

(58) Field of Classification Search
None
See application file for complete search history.

(56) References Cited

U.S. PATENT DOCUMENTS

| | | |
|---|---|---|
| 4,971,908 A | 11/1990 | Kishore et al. |
| 5,188,642 A | 2/1993 | Shah et al. |
| 5,776,760 A | 7/1998 | Barry et al. |
| 6,207,367 B1 | 3/2001 | Helentjaris et al. |
| 6,225,114 B1 | 5/2001 | Eichholtz et al. |
| 6,399,855 B1 | 6/2002 | Beavis |
| 6,803,501 B2 | 10/2004 | Baerson et al. |
| RE38,825 E | 10/2005 | Barry et al. |
| 6,959,617 B2 | 11/2005 | Deppermann |
| RE39,247 E | 8/2006 | Barry et al. |
| 7,134,351 B2 | 11/2006 | Deppermann |
| 7,454,989 B2 | 11/2008 | Deppermann |
| 7,502,113 B2 | 3/2009 | Deppermann et al. |
| 7,591,101 B2 | 9/2009 | Deppermann |
| 7,611,842 B2 | 11/2009 | Deppermann et al. |
| 7,666,644 B2 | 2/2010 | Castle et al. |
| 7,685,768 B2 | 3/2010 | Deppermann |
| 2004/0031072 A1 | 2/2004 | La Rosa et al. |
| 2006/0135758 A1 | 6/2006 | Wu |
| 2010/0086963 A1 | 4/2010 | Deppermann et al. |
| 2010/0099859 A1 | 4/2010 | Malven et al. |

FOREIGN PATENT DOCUMENTS

WO 2008/153804 A2 12/2008

OTHER PUBLICATIONS

Shearin et al. (Dissertation Submitted to the Graduate Faculty of the University of Georgia, (2011), pp. 1-103).*
Soybase.org (accessed on Sep. 25, 2017).*
Shearin, "Enhancing Resistance to Southern Stem Canker and Southern Root-Knot Nematode in Soybean", Master's Thesis, University of Georgia, Aug. 2007, pp. i-90.
Choi et al., "A Soybean Transcript Map: Gene Distribution, Haplotype and Single-Nucleotide Polymorphism Analysis", Genetics, May 2007, pp. 685-696, vol. 176 No. 1.
Grant et al., "SoyBase, the USDA-ARS Soybean Genetics and Genomics Database", Nucleic Acids Research, Jan. 2010, pp. D843-D846, vol. 38 (Database issue).
Hyten et al., "A High Density Integrated Genetic Linkage Map of Soybean and the Development of a 1536 Universal Soy Linkage Panel for Quantitative Trait Locus Mapping", Crop Science, 2010, pp. 960-968, vol. 50 No. 3.
Hyten et al., "High-Throughput SNP Discovery Through Deep Resequencing of a Reduced Representation Library to Anchor and Orient Scaffolds in the Soybean Whole Genome Sequence", BMC Genomics, Jan. 15, 2010, pp. 38, vol. 11.
Keeling, "Measurement of Soybean Resistance to Stem Canker Caused by *Diaporthe phaseolorum* var. *caulivora*", Plant Disease, Mar. 1988, pp. 217-220, vol. 72 No. 3.
Li et al., "Pollen Cryopreservation and Pollen Protoplast Isolation in *Brassica campestris* Var. *purpurea*", Acta Botanica Sinica, 1993, pp. 733-738, vol. 35.
Padgette et al., "Development, Identification, and Characterization of a Glyphosate-Tolerant Soybean Line", Crop Science, 1995, pp. 1451-1461, vol. 35 No. 5.
Pioli et al., "Morphologic, Molecular, and Pathogenic Characterization of Diaporthe Phaseolorum Variability in the Core Soybean-Producing Area of Argentina", Phytopathology, Feb. 2003, pp. 136-146, vol. 93 No. 2.

(Continued)

*Primary Examiner* — Medina A Ibrahim
(74) *Attorney, Agent, or Firm* — Thompson Coburn LLP; William A. Holtz; Amanda J. Carmany-Rampey

(57) ABSTRACT

The present invention provides methods and compositions for the identification and selection of loci modulating phenotypic expression of a stem canker resistance trait in plant breeding. In addition, methods are provided for screening germplasm entries for the performance and expression of this trait.

4 Claims, No Drawings
Specification includes a Sequence Listing.

(56) References Cited

OTHER PUBLICATIONS

Tyagi et al., "Pollen and Glycine Species Survive Cryogenic Exposure", Cryo Letters, Mar.-Apr. 2003, pp. 119-124, vol. 24 No. 2.
Yoon et al., "BARCSoySNP23: A Panel of 23 Selected SNPs for Soybean Cultivar Identification", Theoretical Applied Genetics, Mar. 2007, pp. 885-899, vol. 114 No. 5.
Song et al., "Development and Evaluation of SoySNP50K, a High-Density Genotyping Array for Soybean", PLOS ONE, Jan. 2013, pp. 1-12, vol. 8, No. 1, e54985.

* cited by examiner

SEQUENCE LISTING

```
<160> NUMBER OF SEQ ID NOS: 45

<210> SEQ ID NO 1
<211> LENGTH: 201
<212> TYPE: DNA
<213> ORGANISM: Glycine max

<400> SEQUENCE: 1
gcatctttcg gccgagactg caaaaaagtc tcatttgcta tccgtcagaa tgaaagtctg       60
gtagcatgca atgacgaacg tcgtcatttg caccttcct vgagatgtca gcgtcttccg      120
gtcgagactt taaaaaagtc tcatttgcta tccgtaagac tcaaagcccg atagtatgca      180
ttgactaacg atgtcatttg c                                                201

<210> SEQ ID NO 2
<211> LENGTH: 201
<212> TYPE: DNA
```

<213> ORGANISM: Glycine max

<400> SEQUENCE: 2

```
agctttgaaa gaacaaatgg cttctatgat ggaggccatg ctagggatga atgactaat      60
ggagagtaac gaggccatcg ccgccgccgc tagcatggct vttgaggcag acctgattct     120
cccgactgct gcacaccatc ctgttccaaa cattgtggga cgagggagaa gcacaccagg    180
gcatgtcagc aaccccatc t                                                201
```

<210> SEQ ID NO 3
<211> LENGTH: 201
<212> TYPE: DNA
<213> ORGANISM: Glycine max

<400> SEQUENCE: 3

```
tgctgtcatt agtgattaag aaaagagaag aaaagagctt tatagtaact cataactttg     60
taatcgtttg gttataaaga tcttttcttg gaagtgagtt vtgtcttttg agttgaagaa    120
gatcacctcc tcaatccaac aaggtttttg tggaaatatt ggtgaggttg tatctctctt   180
gctcgttttt tttttgtgta t                                               201
```

<210> SEQ ID NO 4
<211> LENGTH: 201
<212> TYPE: DNA
<213> ORGANISM: Glycine max

<400> SEQUENCE: 4

```
tgactaattg ctacttatat attagttagt atacaccaga caaatggtct attcctgaac     60
gagagttaac atagaggatt taataatgaa agtaatttgt vtattattag tggaatggat    120
ctaaataaag taggtgatta tttggtaaag taatgagtgg agcccacaaa atagaaatgt   180
agcagacaga aaaattaatg a                                               201
```

<210> SEQ ID NO 5
<211> LENGTH: 201
<212> TYPE: DNA
<213> ORGANISM: Glycine max

<400> SEQUENCE: 5

```
gcaaaactag ggtttctgtt tctctttccg aactgagtag cagctctgac catggcagag     60
gaccttactc atatcgctta gttgctcgac caaaccctcc vccccgatgc cattatcatt    120
cgcaccgcca ccgccaccat cgtacttaat cgtatctccc tcactctgca cttccctttc   180
tacctccttt ccatttccac t                                               201
```

<210> SEQ ID NO 6
<211> LENGTH: 201
<212> TYPE: DNA
<213> ORGANISM: Glycine max

<400> SEQUENCE: 6

```
ggacacggcc atacccaatt tggttgctct tgagggggttt cttcgtgtat cacagcaacc    60
catccttcgc acatccaccc cgcgctgata aagctttgat hgatgtgaca tatgggact     120
cctttcactt gcagcctttg cggctggccc gcgcttctct ccctcctttc ttgggcaatc   180
ctccttatgc cggtgcgcgt a                                               201
```

<210> SEQ ID NO 7
<211> LENGTH: 201

<212> TYPE: DNA
<213> ORGANISM: Glycine max

<400> SEQUENCE: 7

```
gaacgttgcg gtagtcaagt agaagagcac ttctctaaca aagggcaagg gataaacaac      60
aaatggcaca acatagacgg cgacaaagcc gatgacaacg dcagagacaa aggttccggt     120
ggagagaatg gcaccgaagc cgatgcggca ttggtcggcg cggagggcaa tgaggggggaa    180
gatgtcgagg gtgctgttgc c                                               201
```

<210> SEQ ID NO 8
<211> LENGTH: 201
<212> TYPE: DNA
<213> ORGANISM: Glycine max

<400> SEQUENCE: 8

```
attttctcaa aggtgtaagc cttttgcgga atccacctgc taagcgcttc cccacacacc      60
gttgttagcc aaggtggcca gccagctgct acttgctccc hctacaaatg ctttgttagg     120
tttgatcttc ttcgttcacc cttcggtcgc caaacctgat catcaccacc accattctct     180
tccttctcct tctcaccatt c                                               201
```

<210> SEQ ID NO 9
<211> LENGTH: 201
<212> TYPE: DNA
<213> ORGANISM: Glycine max

<400> SEQUENCE: 9

```
tatgatgata caggtcatgt gagtaagtga tatgtgtata agcatttgat tgggcttgtt      60
aataaaatgt tatgtaagat tgattcggcc cttcgtaaca haaaaaaaat aattgggaca     120
aagggtgact aataacagta aaaaacctta tagattagtc cttaggtaaa aaaaaatagg     180
ggtgtattta gttactattt t                                               201
```

<210> SEQ ID NO 10
<211> LENGTH: 201
<212> TYPE: DNA
<213> ORGANISM: Glycine max

<400> SEQUENCE: 10

```
ctagtcggta aaaccccctcc ttttttatgt accacccaac cataattgat ggcataccac     60
taaaccatgg ttttcacata accgttaacc ttaataacac dcgtaacact aaaccctaag    120
tattatacta accctaaaca gttcgaacgt aaagtataat acacaattat atgaatttcc    180
aacgtaaagt atagtacatg a                                              201
```

<210> SEQ ID NO 11
<211> LENGTH: 201
<212> TYPE: DNA
<213> ORGANISM: Glycine max

<400> SEQUENCE: 11

```
gactatgtca tgtaacctcc aacctgctta ctggtgtatt ggcttgcata agagagataa      60
tcgtataggt acgccatgc agtggctccc caagcgtacc agtggcagtc atccaggttg     120
ctggggtaga ggtaggcaat gtggacatga gtcaaggact tattaggaaa tatgtattgt    180
tgacaaagtg caaagataa c                                                201
```

<210> SEQ ID NO 12

<211> LENGTH: 201
<212> TYPE: DNA
<213> ORGANISM: Glycine max

<400> SEQUENCE: 12

```
aacctgctta ctggtgtatt ggcttgcata agagagataa tcgtataggt acgcctatgc    60
agtggctccc caagcgtacc ggtggcagtc atccaggttg btggggtaga ggtaggcaat   120
gtggacatga gtcaaggact tattaggaaa tatgtattgt tgacaaagtg caaaagataa   180
cctatggcaa ctcacacgta c                                             201
```

<210> SEQ ID NO 13
<211> LENGTH: 201
<212> TYPE: DNA
<213> ORGANISM: Glycine max

<400> SEQUENCE: 13

```
ccttctacat tattgttgcc aattcgaaca ctgtaaaggg tttgacaatt cccaatttca    60
acaggaaggt taccacttaa attgttctga gtgaggatca baacttctag cttcctaaag   120
taaaaatgct tcatggtata gggccttcaa ggttgtttga atgcagatta agtattttaa   180
gctcagaaat gaatccaagt g                                             201
```

<210> SEQ ID NO 14
<211> LENGTH: 201
<212> TYPE: DNA
<213> ORGANISM: Glycine max

<400> SEQUENCE: 14

```
taattttgtg aagagaggtt ctcaatggta gagtgatttt taagcaattg tgagatgttt    60
gataataggt tggggtggtt cccaaaatgt attgagagtg vttggtgaag gtagggaagt   120
aagcttttgc aactcaaagt gggttggtaa ggagagcttg ggcaagaaat ttaattgaat   180
gtacttacat ttggaacaaa a                                             201
```

<210> SEQ ID NO 15
<211> LENGTH: 201
<212> TYPE: DNA
<213> ORGANISM: Glycine max

<400> SEQUENCE: 15

```
aaaagggaaa ttatagggta tttaaagacc ctaaatcgcc aaaggagcgt tttcaggtga    60
cctcgccaac accaatggcg ccttcacttt ctgcaaaaag htgctgctac acgtaggggt   120
aaagcgctgg tttgaccagc gactccaccc tgcatggcca aagcgccatt gcaggtggcg   180
ataccagtgc tgtcgccagt g                                             201
```

<210> SEQ ID NO 16
<211> LENGTH: 524
<212> TYPE: DNA
<213> ORGANISM: Glycine max

<400> SEQUENCE: 16

```
agcttgcatg cctgcagaaa gatatggagc aatcagatta attaaattca gtaaatgtag    60
gacctccagg tgttcatgtt tcaaaacctt atcttcttta cattcatcag aagtgctcaa   120
agcatttaat ttcagtgcca aagcactgca acttttcagc tcagacaaaa caaacttgct   180
agcttccttg gtaactgtgg aggatttgat agacttgaaa accttctcaa cagattcttg   240
agcacatctg cgtacctaaa aagcaaacaa accacaacac aatttaaaca aavaaaaaat   300
```

```
ccataagctc agagtaatga aatgattaat aggcatggac caatgtctcg aaatcaaagg    360
tcatatcata accaaatgct gattgcattg taaggtaaaa ccatcaccaa atctatacat    420
aattggatat aaacaaggtt taaaactaaa gttgcagaca cattagcagc accaaaaatt    480
gcagaatatt gaaaatagat tcagttgatt cctttttgaaa gtga                    524
```

<210> SEQ ID NO 17
<211> LENGTH: 201
<212> TYPE: DNA
<213> ORGANISM: Glycine max

<400> SEQUENCE: 17

```
ccattatatg aatcagagtt tcagagaaaa gagaactttt agaagagaga cattttagta    60
agaagagagt attattggat tcagtgtgtc ttaacataca vactcatcct ctttatatag   120
gagaggattc gaaactaaca tccaaaatct tatccatgaa aggataaaag tgtcgtgcta   180
ataacacaaa ggtcacgggt t                                             201
```

<210> SEQ ID NO 18
<211> LENGTH: 201
<212> TYPE: DNA
<213> ORGANISM: Glycine max

<400> SEQUENCE: 18

```
ttagaagaga gacattttag taagaagaga gtattattgg attcagtgtg tcttaacata    60
cagactcatc ctctttatat aggagaggat tcgaaactaa hatccaaaat cttatccatg   120
aaaggataaa agtgtcgtgc taataacaca aaggtcacgg gtttgagacc tgcatgggcc   180
aatctatatg gggctataca g                                             201
```

<210> SEQ ID NO 19
<211> LENGTH: 201
<212> TYPE: DNA
<213> ORGANISM: Glycine max

<400> SEQUENCE: 19

```
tagtaagaag agagtattat tggattcagt gtgtcttaac atacagactc atcctcttta    60
tataggagag gattcgaaac taacatccaa aatcttatcc dtgaaaggat aaaagtgtcg   120
tgctaataac acaaaggtca cgggtttgag acctgcatgg gccaatctat atggggctat   180
acagattgtc aatctgtatg g                                             201
```

<210> SEQ ID NO 20
<211> LENGTH: 202
<212> TYPE: DNA
<213> ORGANISM: Glycine max

<400> SEQUENCE: 20

```
tacagactca tcctctttat ataggagagg attcgaaact aacatccaaa atcttatcca    60
tgaaaggata aaagtgtcgt gctaataaca caaaggtcac ddggtttgag acctgcatgg   120
gccaatctat atggggctat acagattgtc aatctgtatg gctatacgt aaggacaatg   180 ttggaattaa taaaaagttg aa                                            202
```

<210> SEQ ID NO 21
<211> LENGTH: 201
<212> TYPE: DNA
<213> ORGANISM: Glycine max

<400> SEQUENCE: 21

```
aggattcgaa actaacatcc aaaatcttat ccatgaaagg ataaaagtgt cgtgctaata      60
acacaaaggt cacgggtttg agacctgcat gggccaatct dtatggggct atacagattg     120
tcaatctgta tgggctatac gtaaggacaa tgttggaatt aataaaaagt gaatgatgt      180
atatgagatt tgaatggtgt a                                               201
```

<210> SEQ ID NO 22
<211> LENGTH: 24
<212> TYPE: DNA
<213> ORGANISM: Glycine max

<400> SEQUENCE: 22

```
agcaaacaaa ccacaacaca attt                                             24
```

<210> SEQ ID NO 23
<211> LENGTH: 28
<212> TYPE: DNA
<213> ORGANISM: Glycine max

<400> SEQUENCE: 23

```
tccatgccta ttaatcattt cattactc                                         28
```

<210> SEQ ID NO 24
<211> LENGTH: 14
<212> TYPE: DNA
<213> ORGANISM: Glycine max

<400> SEQUENCE: 24

```
acaaacaaaa aatc                                                        14
```

<210> SEQ ID NO 25
<211> LENGTH: 15
<212> TYPE: DNA
<213> ORGANISM: Glycine max

<400> SEQUENCE: 25

```
aacaaagaaa aaatc                                                       15
```

<210> SEQ ID NO 26
<211> LENGTH: 201
<212> TYPE: DNA
<213> ORGANISM: Glycine max

<400> SEQUENCE: 26

```
gagtgtgctc agtgggggag ggagtgttcc ggcgacaaag gcatctgctg agacctggca      60
gcaaatggtg aatcagctgc aaaaggcagc attgtctact ygccacggga ttccgatgat     120
ttatggtata gatgcagttc atggacacaa caatgtctat aatgctacca tttttcctca     180
caatgttggg ctaggagtta c                                               201
```

<210> SEQ ID NO 27
<211> LENGTH: 201
<212> TYPE: DNA
<213> ORGANISM: Glycine max

<400> SEQUENCE: 27

```
caatattctc attgaagcaa ttttcttact ggaaagttta tgagagcact cggacccaa       60
tatctcagag cagcaaggtc atatgctcta gctgctgcct yttcatcatc atatgcccct     120
gtttgaaaac catcagcaac aaagcagcaa gttcattaca aaaccagaag aaaggaaaag     180
```

```
aataaggagg gggaggggc a                                                        201

<210> SEQ ID NO 28
<211> LENGTH: 201
<212> TYPE: DNA
<213> ORGANISM: Glycine max

<400> SEQUENCE: 28
acatatttaa ctaggaacct cacaaatatc aatttataaa actatttagt gatatgagca             60
atgaaagaat ccatttccat gcgagaaact ccatcttcat mcatggacct atggatggcg            120
tttttaagcc taactgctct ctctcgcatc tcatcacctt catttgtttc catcaacctt            180
ctcacagtat tctcaacaac t                                                      201

<210> SEQ ID NO 29
<211> LENGTH: 170
<212> TYPE: DNA
<213> ORGANISM: Glycine max

<400> SEQUENCE: 29
atctcacgct ttctaattcc ttataattaa aaatctgaac ctaccaattt ttctttgtgt             60
ctggagaggc tttaaaaatt taacctacaa ctgagcttgc ytccaaattt cttataatta            120
aacttcttgc acaaactctt atctatcaga taacaatttt tttgctgacg                       170

<210> SEQ ID NO 30
<211> LENGTH: 24
<212> TYPE: DNA
<213> ORGANISM: Glycine max

<400> SEQUENCE: 30
aaatggtgaa tcagctgcaa aagg                                                    24

<210> SEQ ID NO 31
<211> LENGTH: 25
<212> TYPE: DNA
<213> ORGANISM: Glycine max

<400> SEQUENCE: 31
tgttgtgtcc atgaactgca tctat                                                   25

<210> SEQ ID NO 32
<211> LENGTH: 14
<212> TYPE: DNA
<213> ORGANISM: Glycine max

<400> SEQUENCE: 32
cccgtggcaa gtag                                                               14

<210> SEQ ID NO 33
<211> LENGTH: 15
<212> TYPE: DNA
<213> ORGANISM: Glycine max

<400> SEQUENCE: 33
tcccgtggcg agtag                                                              15

<210> SEQ ID NO 34
<211> LENGTH: 22
<212> TYPE: DNA
<213> ORGANISM: Glycine max
```

```
<400> SEQUENCE: 34
tcagagcagc aaggtcatat gc                                         22

<210> SEQ ID NO 35
<211> LENGTH: 24
<212> TYPE: DNA
<213> ORGANISM: Glycine max

<400> SEQUENCE: 35
tgctttgttg ctgatggttt tcaa                                       24

<210> SEQ ID NO 36
<211> LENGTH: 16
<212> TYPE: DNA
<213> ORGANISM: Glycine max

<400> SEQUENCE: 36
ctgctgcctt ttcatc                                                16

<210> SEQ ID NO 37
<211> LENGTH: 15
<212> TYPE: DNA
<213> ORGANISM: Glycine max

<400> SEQUENCE: 37
tgctgcctct tcatc                                                 15

<210> SEQ ID NO 38
<211> LENGTH: 25
<212> TYPE: DNA
<213> ORGANISM: Glycine max

<400> SEQUENCE: 38
agaatccatt tccatgcgag aaact                                      25

<210> SEQ ID NO 39
<211> LENGTH: 25
<212> TYPE: DNA
<213> ORGANISM: Glycine max

<400> SEQUENCE: 39
cgagagagag cagttaggct taaaa                                      25

<210> SEQ ID NO 40
<211> LENGTH: 19
<212> TYPE: DNA
<213> ORGANISM: Glycine max

<400> SEQUENCE: 40
ccatcttcat acatggacc                                             19

<210> SEQ ID NO 41
<211> LENGTH: 18
<212> TYPE: DNA
<213> ORGANISM: Glycine max

<400> SEQUENCE: 41
catcttcatc catggacc                                              18

<210> SEQ ID NO 42
<211> LENGTH: 24
<212> TYPE: DNA
<213> ORGANISM: Glycine max
```

```
<400> SEQUENCE: 42
tttctttgtg tctggagagg cttt                                          24

<210> SEQ ID NO 43
<211> LENGTH: 35
<212> TYPE: DNA
<213> ORGANISM: Glycine max

<400> SEQUENCE: 43
tctgatagat aagagtttgt gcaagaagtt taatt                              35

<210> SEQ ID NO 44
<211> LENGTH: 17
<212> TYPE: DNA
<213> ORGANISM: Glycine max

<400> SEQUENCE: 44
ctgagcttgc ctccaaa                                                  17

<210> SEQ ID NO 45
<211> LENGTH: 17
<212> TYPE: DNA
<213> ORGANISM: Glycine max

<400> SEQUENCE: 45
ctgagcttgc ttccaaa                                                  17
```

MOLECULAR MARKERS ASSOCIATED WITH STEM CANKER RESISTANCE IN SOYBEAN

CROSS-REFERENCE TO RELATED APPLICATIONS

This application is a 35 U.S.C. § 371 National Phase application of International Patent Application No. PCT/US2012/052766, filed Aug. 29, 2012 and incorporated herein by reference in its entirety, which claims the benefit of U.S. Provisional Patent Application No. 61/529,889, filed Aug. 31, 2011, which is incorporated herein by reference in its entirety.

INCORPORATION OF SEQUENCE LISTING

A sequence listing containing the file named "46_21_57834.txt" which is 12,956 bytes (measured in MS-Windows®) and created on Aug. 22, 2012, comprises 45 nucleotide sequences, is provided herewith via the USPTO's EFS system and is herein incorporated by reference in its entirety.

BACKGROUND OF INVENTION

Soybean, *Glycine max* (L.) Merril, is a major economic crop worldwide and is a primary source of vegetable oil and protein (Sinclair and Backman, *Compendium of Soybean Diseases*, 3$^{rd}$ Ed. APS Press, St. Paul, Minn., p. 106, (1989)). The growing demand for low cholesterol and high fiber diets has also increased soybean's importance as a health food.

Soybean varieties grown in the United States have a narrow genetic base. Six introductions, 'Mandarin,' 'Manchu,' 'Mandarin' (Ottawa), "Richland,' 'AK' (Harrow), and 'Mukden,' contributed nearly 70% of the germplasm represented in 136 cultivar releases. To date, modern day cultivars can be traced back from these six soybean strains from China. In a study conducted by Cox et al., *Crop Sci.* 25:529-532 (1988), the soybean germplasm is comprised of 90% adapted materials, 9% unadapted, and only 1% from exotic species. The genetic base of cultivated soybean could be widened through exotic species. In addition, exotic species may possess such key traits as disease, stress, and insect resistance.

Soybean stem canker is caused by *Diaporthe phaseolorum* sp. and results in reductions in yield.

There is a need in the art of plant breeding to identify additional markers linked to quantitative trait loci associated with stem canker resistance in soybean. There is in particular a need for numerous markers that are closely associated with stem canker resistance QTLs in soybean that permit introgression of the stem canker resistance QTL in the absence of extraneous linked DNA from the source germplasm containing the QTL. Additionally, there is a need for rapid, cost-efficient method to assay the absence or presence of stem canker resistance loci in soybean.

SUMMARY OF INVENTION

In certain embodiments, the present invention provides methods for producing stem canker resistance in soybean plants, stem canker resistant soybean plants, and polymorphic nucleic acids useful for identifying or producing stem canker resistant soybean plants. In certain embodiments, the present invention further relates to methods to determine the presence or absence of quantitative trait loci conferring stem canker resistance in soybean plants, including but not limited to exotic germplasm, populations, lines, elite lines, cultivars and varieties. In certain embodiments, the invention relates to methods that provide for identification of molecular markers associated with stem canker resistance quantitative trait loci (QTL). In certain embodiments, the present invention relates to the use of molecular markers to screen and select for stem canker resistance within soybean plants, including but not limited to exotic germplasm, populations, lines, elite lines, and varieties.

Methods of identifying a soybean plant that comprises a genotype associated with a stem canker resistance phenotype are provided. In certain embodiments, these methods of identifying a soybean plant that comprises a genotype associated with a stem canker resistance phenotype can comprise: detecting in the soybean plant an allele in at least one stem canker resistance marker locus associated with the stem canker resistance phenotype wherein the stem canker resistance marker locus is in a linkage group D1b genomic region flanked by or including:

a) loci NGMAX008369670 and NGMAX008369689;
b) loci NGMAX008369675 and loci NGMAX008369689;
c) loci NGMAX008369673 and loci NGMAX008369689;
d) loci NGMAX008369676 and loci NGMAX008369689;
e) loci NGMAX008369683 and loci NGMAX008369689;
f) loci NGMAX008369675 and loci NGMAX008369686;
g) loci NGMAX008369673 and loci NGMAX008369686;
h) loci NGMAX008369676 and loci NGMAX008369686; or,
i) loci NGMAX008369683 and loci NGMAX008369686;
and,
denoting that the plant comprises a genotype associated with a stem canker resistance phenotype are provided. In certain embodiments of the methods, the methods can further comprise the step of selecting the denoted plant from a population of plants. In certain embodiments of the methods, the selected plant exhibits a stem canker resistance phenotype. In certain embodiments of any of the aforementioned methods, the genotype associated with a stem canker resistance phenotype comprises at least one polymorphic allele of a marker selected from the group consisting loci NGMAX008369683 (SEQ ID NO: 15) and loci NGMAX008369686 (SEQ ID NO: 17). In certain embodiments of any of the aforementioned methods, the genotype associated with a stem canker resistance phenotype comprises at least one polymorphic allele of a marker flanked by loci NGMAX008369683 (SEQ ID NO: 15) and loci NGMAX008369686 (SEQ ID NO: 17). In certain embodiments of any of the aforementioned methods, the genotype associated with a stem canker resistance phenotype comprises at least one polymorphic allele of at least one marker selected from the group consisting of NGMAX009107570 (SEQ ID NO: 28), NGMAX009107770 (SEQ ID NO: 26), NGMAX009107970 (SEQ ID NO: 27), and NGMAX009108170 (SEQ ID NO: 29), and NS0092616 (SEQ ID NO: 16). The aforementioned loci and/or markers refer to SEQ ID NO and sequences provided herewith in Tables 1, 2, 3, 4, and 14.

Also provided are methods for obtaining a soybean plant comprising in its genome at least one stem canker resistance locus. In certain embodiments, the methods for obtaining a soybean plant comprising in its genome at least one stem canker resistance locus can comprise genotyping a plurality of soybean plants with respect to at least one stem canker resistance locus in a linkage group D1b genomic region flanked by or including:

(a) loci NGMAX008369670 and NGMAX008369689;
(b) loci NGMAX008369675 and loci NGMAX008369689;
(c) loci NGMAX008369673 and loci NGMAX008369689;
(d) loci NGMAX008369676 and loci NGMAX008369689;
(e) loci NGMAX008369683 and loci NGMAX008369689;
(f) loci NGMAX008369675 and loci NGMAX008369686;
(g) loci NGMAX008369673 and loci NGMAX008369686;
(h) loci NGMAX008369676 and loci NGMAX008369686; or,
(i) loci NGMAX008369683 and loci NGMAX008369686; and, selecting a soybean plant comprising in its genome at least one stem canker resistance locus comprising a genotype associated with a stem canker resistance phenotype are provided. In certain embodiments of the methods, the selected soybean plant exhibits stem canker resistance. In certain embodiments of the methods, the methods can further comprise assaying the selected plant for a stem canker resistance phenotype. In certain embodiments of any of the aforementioned methods, the methods can further comprise the step of assaying for the presence of at least one additional marker, wherein the additional marker is either linked or unlinked to a linkage group D1b genomic region flanked by any one of the loci sets of (a)-(h), or (i). In certain embodiments of any of the aforementioned methods, the stem canker resistance locus is genotyped for at least one polymorphic allele of a marker selected from the group consisting of loci NGMAX008369683 (SEQ ID NO: 15) and loci NGMAX008369686 (SEQ ID NO: 17). In certain embodiments of any of the aforementioned methods, the stem canker resistance locus is genotyped for at least one polymorphic allele of at least one marker selected from the group consisting of NGMAX009107570 (SEQ ID NO: 28), NGMAX009107770 (SEQ ID NO: 26), NGMAX009107970 (SEQ ID NO: 27), and NGMAX009108170 (SEQ ID NO: 29), and NS0092616 (SEQ ID NO: 16). The aforementioned loci and/or markers refer to SEQ ID NO and sequences provided herewith in Tables 1, 2, 3, 4, and 14.

Also provided are methods for identifying a soybean plant comprising in its genome at least one introgressed stem canker resistance locus. In certain embodiments, methods for identifying a soybean plant comprising in its genome at least one introgressed stem canker resistance locus can comprise crossing a first soybean plant with a second soybean plant comprising: (i) a stem canker resistance locus in a linkage group D1b genomic region flanked by or including:

a) loci NGMAX008369670 and NGMAX008369689;
b) loci NGMAX008369675 and loci NGMAX008369689;
c) loci NGMAX008369673 and loci NGMAX008369689;
d) loci NGMAX008369676 and loci NGMAX008369689;
e) loci NGMAX008369683 and loci NGMAX008369689;
f) loci NGMAX008369675 and loci NGMAX008369686;
g) loci NGMAX008369673 and loci NGMAX008369686;
h) loci NGMAX008369676 and loci NGMAX008369686; or,
i) loci NGMAX008369683 and loci NGMAX008369686; and, (ii) at least one additional polymorphic locus located outside of the linkage group D1b region, to obtain a population of soybean plants segregating for the stem canker resistance loci and the at least one additional polymorphic locus; and detecting the polymorphic nucleic acid in at least one soybean plant from the population of soybean plants, wherein the one soybean plant lacks the additional polymorphic locus, thereby identifying a soybean plant comprising in its genome at least one introgressed stem canker resistance locus, are provided. In certain embodiments, the methods can further comprise the step of selecting the one soybean plant, thereby obtaining a soybean plant comprising in its genome at least one introgressed stem canker resistance locus. In certain embodiments of the methods, the polymorphic nucleic acid in the linkage group D1b region associated with stem canker resistance is detected with at least one marker selected from the group consisting of loci NGMAX008369683 (SEQ ID NO: 17) and loci NGMAX008369686 (SEQ ID NO: 17). In certain embodiments of the methods, the polymorphic nucleic acid in the linkage group D1b region associated with stem canker resistance is detected with at least one marker flanked by loci NGMAX008369683 (SEQ ID NO: 17) and loci NGMAX008369686 (SEQ ID NO: 17). In certain embodiments, the polymorphic nucleic acid in the linkage group D1b region associated with stem canker resistance is detected with marker selected from the group consisting of NGMAX009107570 (SEQ ID NO: 28), NGMAX009107770 (SEQ ID NO: 26), NGMAX009107970 (SEQ ID NO: 27), and NGMAX009108170 (SEQ ID NO: 29), and NS0092616 (SEQ ID NO: 16). In certain embodiments of any of the aforementioned methods, the identified or the selected plant is stem canker resistant. In certain embodiments of any of the aforementioned methods, the identified or the selected plant is assayed for stem canker resistance. In certain embodiments of any of the aforementioned methods, the additional polymorphic locus is detected with a genotypic marker, a phenotypic marker, or both. In certain embodiments of any of the aforementioned methods, the additional polymorphic locus is a linked polymorphic locus located on linkage group D1b but not within the linkage group D1b genomic region flanked by or including any one of loci sets (a)-(h), or (i). In certain embodiments of the aforementioned methods, the linked polymorphic locus is detected with at least one marker that is located within a genomic region of the soybean genome flanked by or that includes loci: a) NGMAX008369622 and NGMAX008369668; and/or, b) NGMAX008369690 and NGMAX008369698. In certain embodiments of the aforementioned methods, the polymorphic locus is detected with at least one marker selected from the group consisting of NGMAX008369622, NGMAX008369632, NGMAX008369668, NGMAX008369642, NGMAX008369650, NGMAX008369665, NGMAX008369690, NGMAX008369699, and NGMAX008369698. The aforementioned loci and/or markers refer to SEQ ID NO and sequences provided herewith in Tables 1, 2, 3, 4, and 7.

Also provided herein are soybean plants obtainable by any of the aforementioned methods.

Soybean plants comprising plants comprising linkage group D1b genomic regions associated with a stem canker resistance phenotype wherein immediately adjacent genomic regions and/or one or more adjacent genomic regions characteristic of soybean germplasms that lack the genomic regions associated with a stem canker resistance phenotype and/or that are distinct from the germplasm from which the genomic region is derived are also provided. In certain embodiments, a soybean plant comprising i) a stem canker resistance locus in a linkage group D1b region that is flanked by or includes:

a) loci NGMAX008369670 and NGMAX008369689;
b) loci NGMAX008369675 and loci NGMAX008369689;
c) loci NGMAX008369673 and loci NGMAX008369689;
d) loci NGMAX008369676 and loci NGMAX008369689;
e) loci NGMAX008369683 and loci NGMAX008369689;
f) loci NGMAX008369675 and loci NGMAX008369686;
g) loci NGMAX008369673 and loci NGMAX008369686;
h) loci NGMAX008369676 and loci NGMAX008369686; or,
i) loci NGMAX008369683 and loci NGMAX008369686; and, (ii) one or more polymorphic loci comprising alleles or combinations of alleles that are not found in a stem canker resistant soybean varieties harboring the stem canker resistance locus, and that are linked to the stem canker resistance locus, wherein the soybean plant is stem canker resistant, are provided. In certain embodiments, the stem canker resistance locus comprises an introgressed region of the soybean genome that is flanked by loci NGMAX008369683 and loci NGMAX008369686. In certain embodiments of any of the aforementioned stem canker resistant soybean plants, the soybean plant comprises an allele of at least one marker selected from the group consisting of loci NGMAX008369683 and loci NGMAX008369686 that is associated with stem canker resistance. In certain embodiments of any of the aforementioned stem canker resistant soybean plants, the soybean plant comprises an allele of at least one marker flanked by loci NGMAX008369683 and loci NGMAX008369686 that is associated with stem canker resistance. In certain embodiments of any of the aforementioned stem canker resistant soybean plants, the soybean plant comprises an allele of at least one marker selected from the group consisting of NGMAX009107570 (SEQ ID NO: 28), NGMAX009107770 (SEQ ID NO: 26), NGMAX009107970 (SEQ ID NO: 27), and NGMAX009108170 (SEQ ID NO: 29), and NS0092616 (SEQ ID NO: 16) that is associated with stem canker resistance. In certain embodiments of any of the aforementioned stem canker resistant soybean plants, the linked polymorphic loci comprising alleles or combinations of alleles that are not found in a stem canker resistant soybean varieties harboring the stem canker resistance locus comprise alleles of at least one marker that is located within a genomic region of the soybean genome flanked by or that includes loci: a) NGMAX008369622 and NGMAX008369668; and/or, b) NGMAX008369690 and NGMAX008369698. The aforementioned loci and/or markers refer to SEQ ID NO and sequences provided herewith in Tables 1, 2, 3, 4, and 7.

Also provided herewith are isolated nucleic acid molecules comprising a nucleic acid molecule selected from the group consisting of an allele of marker NS0092616 (SEQ ID NO: 16) that is associated with stem canker resistance or stem canker sensitivity. In certain embodiments, the nucleic acid can further comprise a detectable moiety. In certain embodiments, the detectable moiety can be selected from the group consisting of a chromophore, a fluorophore, and a hapten. The aforementioned nucleic acids refer to SEQ ID NO:16 and associated sequences provided herewith in Tables 1, 2, 3, 4, and 7.

Also, methods of producing a population of soybean plants with a stem canker resistance phenotype are provided. In certain embodiments, these methods of producing a population of soybean plants comprising a genotype associated with a stem canker resistance phenotype can comprise: providing a first population of soybean plants, detecting in the soybean plants of the first population an allele in at least one stem canker resistance marker locus associated with the stem canker resistance phenotype wherein the stem canker resistance marker locus is in a linkage group D1b genomic region flanked by or including:

a) loci NGMAX008369670 and NGMAX008369689;
b) loci NGMAX008369675 and loci NGMAX008369689;
c) loci NGMAX008369673 and loci NGMAX008369689;
d) loci NGMAX008369676 and loci NGMAX008369689;
e) loci NGMAX008369683 and loci NGMAX008369689;
f) loci NGMAX008369675 and loci NGMAX008369686;
g) loci NGMAX008369673 and loci NGMAX008369686;
h) loci NGMAX008369676 and loci NGMAX008369686; or,
i) loci NGMAX008369683 and loci NGMAX008369686;

selecting one or more soybean plants exhibiting an allele in the at least one stem canker resistance locus from the first population of soybean plants; and producing offspring from the one or more selected soybean plants.

Further areas of applicability will become apparent from the description provided herein. It should be understood that the description and specific examples are intended for purposes of illustration only and are not intended to limit the scope of the present disclosure.

DESCRIPTION OF INVENTION

I. Definitions

As used herein, an "allele" refers to one of two or more alternative forms of a genomic sequence at a given locus on a chromosome. When all the alleles present at a given locus on a chromosome are the same, that plant is homozygous at that locus. If the alleles present at a given locus on a chromosome differ, that plant is heterozygous at that locus.

As used herein, the term "bulk" refers to a method of managing a segregating population during inbreeding that involves growing the population in a bulk plot, harvesting the self pollinated seed of plants in bulk, and using a sample of the bulk to plant the next generation.

As used herein, the term "comprising" means "including but not limited to".

As used herein, the term "denoting" when used in reference to a plant genotype refers to any method whereby a plant is indicated to have a certain genotype. Such indications of a certain genotype include, but are not limited to, any method where a plant is physically marked or tagged. Physical markings or tags that can be used include, but are not limited to, a barcode, a radio-frequency identification (RFID), a label or the like. Indications of a certain genotype also include, but are not limited to, any entry into any type of written or electronic database whereby the plant's genotype is provided.

As used herein, the term "locus" refers to a position on a genomic sequence that is usually found by a point of reference; e.g., a short DNA sequence that is a gene, or part of a gene or intergenic region. A locus may refer to a nucleotide position at a reference point on a chromosome, such as a position from the end of the chromosome.

As used herein, "linkage group D1b" corresponds to the soybean linkage group D1b described in Choi, et al., Genetics. 2007 May; 176(1): 685-696. Linkage group D1b, as used herein, also corresponds to soybean chromosome 2 (as described on the World Wide Web at soybase.org/LG2Xsome.php).

As used herein, "polymorphism" means the presence of one or more variations of a nucleic acid sequence at one or more loci in a population of at least two members. The variation can comprise but is not limited to one or more nucleotide base substitutions, the insertion of one or more nucleotides, a nucleotide sequence inversion, and/or the deletion of one or more nucleotides.

As used herein, "genotype" means the genetic component of the phenotype and it can be indirectly characterized using markers or directly characterized by nucleic acid sequencing.

As used herein, the term "introgressed", when used in reference to a genetic locus, refers to a genetic locus that has been introduced into a new genetic background. Introgression of a genetic locus can thus be achieved through both plant breeding methods or by molecular genetic methods. Such molecular genetic methods include, but are not limited to, various plant transformation techniques and/or methods that provide for homologous recombination, non-homologous recombination, site-specific recombination, and/or genomic modifications that provide for locus substitution or locus conversion. In certain embodiments, introgression could thus be achieved by substitution of a stem canker susceptibility locus with a corresponding stem canker resistance locus or by conversion of a locus from a stem canker susceptible genotype to a stem canker resistance genotype.

As used herein, "linkage" refers to relative frequency at which types of gametes are produced in a cross. For example, if locus A has genes "A" or "a" and locus B has genes "B" or "b" and a cross between parent I with AABB and parent B with aabb will produce four possible gametes where the genes are segregated into AB, Ab, aB and ab. The null expectation is that there will be independent equal segregation into each of the four possible genotypes, i.e. with no linkage ¼ of the gametes will be of each genotype. Segregation of gametes into a genotypes differing from ¼ are attributed to linkage.

As used herein, the termed "linked", when used in the context of markers and/or genomic regions, means that the markers and/or genomic regions are located on the same linkage group or chromosome.

As used herein, "marker" means a detectable characteristic that can be used to discriminate between organisms. Examples of such characteristics include, but are not limited to, genetic markers, biochemical markers, fermentation yield, fermentation efficiency, energy yield, secondary compounds, metabolites, morphological characteristics, and agronomic characteristics.

As used herein, "marker assay" means a method for detecting a polymorphism at a particular locus using a particular method. Marker assays thus include, but are not limited to, measurement of at least one phenotype (such as seed color, flower color, or other visually detectable trait as well as any biochemical trait), restriction fragment length polymorphism (RFLP), single base extension, electrophoresis, sequence alignment, allelic specific oligonucleotide hybridization (ASO), random amplified polymorphic DNA (RAPD), microarray-based polymorphism detection technologies, and the like.

As used herein, "phenotype" means the detectable characteristics of a cell or organism which can be influenced by gene expression.

As used herein, the phrase "isolated nucleic acid molecule", be it a naturally occurring molecule or otherwise, refers to a nucleic acid molecule where the covalent bonds between that nucleic acid and other native nucleic acids that adjoin the isolated nucleic acid in its naturally occurring state have been broken or have been replaced with covalent bonds to non-native nucleic acids. An isolated nucleic acid molecule can be the predominant species present in a preparation. In certain embodiments, an isolated nucleic acid molecule can also be at least about 60% free, at least about 75% free, at least about 90% free, and at least about 95% free from other molecules (exclusive of solvent). The phrase ""isolated nucleic acid molecule" thus does not encompass nucleic acid molecules present in their native chromosomal locations.

As used herein, "quantitative trait locus (QTL)" means a locus that controls to some degree numerically representable traits that are usually continuously distributed.

As used herein, the term "soybean" means *Glycine max* and includes all plant varieties that can be bred with soybean, including wild soybean species. In certain embodiments, soybean plants from the species *Glycine max* and the subspecies *Glycine max* L. ssp. *max* or *Glycine max* ssp. *formosana* can be genotyped using the compositions and methods of the present invention. In an additional aspect, the soybean plant is from the species *Glycine soja*, otherwise known as wild soybean, can be genotyped using these compositions and methods. Alternatively, soybean germplasm derived from any of *Glycine max, Glycine max* L. ssp. *max, Glycine max* ssp. Formosana, and/or *Glycine soja* can be genotyped using compositions and methods provided herein.

As used herein, the term "single nucleotide polymorphism," also referred to by the abbreviation "SNP," means a polymorphism at a single site wherein the polymorphism constitutes any or all of a single base pair change, an insertion of one or more base pairs, and/or a deletion of one or more base pairs.

As used herein, the phrase "soybean stem canker" refers to any stem canker that is found on a soybean plant. Stem cankers found on soybean include, but are not limited to, *Diaporthe phaseolorum* f. sp. *meridionalis* (DPM).

As used herein, the phrase "soybean stem canker resistance" refers to any form of resistance to a stem canker that can infect a soybean plant.

As used herein, the term "tolerance", when used in the context of stem canker resistance, refers to the ability of a soybean plant to exhibit a reduction in deleterious effects caused by stem canker infection.

II. Description of the Invention: Overview

In accordance with the present invention, Applicants have discovered genomic regions, associated markers, and associated methods for identifying and associating genotypes that effect a stem canker resistance trait. For example, in one embodiment, a method of the invention comprises screening.

The use of markers to infer a phenotype of interest results in the economization of a breeding program by substituting costly, time—intensive phenotyping assays with genotyping assays. Further, breeding programs can be designed to explicitly drive the frequency of specific, favorable phenotypes by targeting particular genotypes (U.S. Pat. No. 6,399, 855). Fidelity of these associations may be monitored continuously to ensure maintained predictive ability and, thus, informed breeding decisions (US Patent Application 2005/ 0015827). In this case, costly, time-intensive phenotyping assays required for determining if a plant or plants contains a genomic region associated with a stem canker resistance phenotype can be supplanted by genotypic assays that provide for identification of a plant or plants that contain the desired genomic region.

III. A Genomic Region Associated with a Stem Canker Resistance Phenotype

Provided herewith is a soybean genomic region that is shown herein to be associated with a desirable stem canker resistance phenotype when present in certain allelic forms.

A soybean genomic region provided that can be associated with a desirable stem canker resistance phenotype when present in certain allelic forms is located on the telomere proximal end of the short arm of soybean linkage group D1b (chromosome 2). A series of markers useful in practicing the methods of this invention are provided herewith in Table 1 and Table 2. Additional markers useful in the practice of the invention are provided herewith in Tables 3 and 4 of. Tables 3 and 4 provide the Table 1 and Table 2 markers, additional nucleic acid markers or loci that have been disclosed in various databases, the relative positions of the markers on a physical map of linkage group D1b (soybean chromosome 2), and sources for the markers.

TABLE 1

Markers spanning a genomic region associated with a desirable stem canker resistance phenotype

| Marker or Locus Name | SEQ ID NO: | Map Position [1] | Allelic form(s) Associated with Stem Canker Resistance Phenotype [2] |
| --- | --- | --- | --- |
| NGMAX008369670 | 1 | 19,007,046 | GG |
| NGMAX008369671 | 2 | 21,409,115 | AA |
| NGMAX008369675 | 3 | 23,428,066 | GG |
| NGMAX008369672 | 4 | 27,316,222 | GG |
| NGMAX008369673 | 5 | 28,450,255 | GG |
| NGMAX008369674 | 6 | 32,813,596 | CC |
| NGMAX008369676 | 7 | 32,982,299 | AA |
| NGMAX008369677 | 8 | 33,592,314 | TT |
| NGMAX008369680 | 9 | 34,212,327 | TT |
| NGMAX008369678 | 10 | 34,255,783 | AA |
| NGMAX008369679 | 11 | 34,297,519 | GG |
| NGMAX008369681 | 12 | 34,297,519 | CC |
| NGMAX008369682 | 13 | 35,077,968 | TT |
| NGMAX008369684 | 14 | 35,163,509 | AA |
| NGMAX008369683 | 15 | 36,290,051 | TT |
| NS0092616 | 16 | 40,184,874 | GG [3] |
| NGMAX008369686 | 17 | 42,379,943 | GG |
| NGMAX008369687 | 18 | 42,379,943 | CC |
| NGMAX008369685 | 19 | 42,379,943 | AA |

TABLE 1-continued

Markers spanning a genomic region associated with a desirable stem canker resistance phenotype

| Marker or Locus Name | SEQ ID NO: | Map Position [1] | Allelic form(s) Associated with Stem Canker Resistance Phenotype [2] |
| --- | --- | --- | --- |
| NGMAX008369688 | 20 | 42,379,943 | GG |
| NGMAX008369689 | 21 | 42,379,943 | AA |

[1] The relative positions of the 5' telomere proximal nucleotide of the listed markers or loci based on nucleotide positions on a physical map of soybean linkage group D1b (chromosome 2) of Table 3 (Appendix to the Specification) are provided where nucleotide position 0 (zero) is telomere proximal and nucleotide position 42,379,943 is centromere proximal. Polymorphic nucleotide bases are designated in the sequence listing provided herewith according to the WIPO Standard ST.25 (1998), as follows: r = g or a (purine); y = t/u or c (pyrimidine); m = a or c; (amino); k = g or t/u (keto); s = g or c (strong interactions 3 H-bonds); w = a or t/u (weak interactions 2H-bonds); b = g or c or t/u (not a); d = a or g or t/u (not c); h = a or c or t/u (not g); v = a or g or c (not t, not u); and n = a or g or c or t/u (unknown, or other; any.)
[2] Both the maternal and paternal alleles of the single nucleotide polymorphisms that can be associated with a stem canker resistance phenotype are shown.
[3] The identified polymorphic allele of marker NS0092616 is/are located at nucleotide 293 of SEQ ID NO: 16.

TABLE 2

Markers spanning a genomic region associated with a desirable stem canker resistance phenotype in an updated physical map

| Marker or Locus Name | SEQ ID NO: | Updated Map Position [1] | Allelic form(s) Associated with Stem Canker Resistance Phenotype [2] |
| --- | --- | --- | --- |
| NGMAX008369670 | 1 | 19,096,714 | GG |
| NGMAX008369671 | 2 | 21,422,629 | AA |
| NGMAX008369675 | 3 | 23,739,140 | GG |
| NGMAX008369672 | 4 | 27,331,328 | GG |
| NGMAX008369673 | 5 | 28,463,620 | GG |
| NGMAX008369674 | 6 | 32,862,267 | CC |
| NGMAX008369676 | 7 | 33,024,826 | AA |
| NGMAX008369677 | 8 | 33,608,159 | TT |
| NGMAX008369680 | 9 | 34,235,541 | TT |
| NGMAX008369678 | 10 | 34,262,903 | AA |
| NGMAX008369679 | 11 | 34,308,875 | GG |
| NGMAX008369681 | 12 | 34,308,895 | CC |
| NGMAX008369682 | 13 | 35,080,156 | TT |
| NGMAX008369684 | 14 | 35,201,653 | AA |
| NGMAX008369683 | 15 | 36,311,905 | TT |
| NGMAX009107770 | 26 | 37,347,910 | CC [4] |
| NGMAX009107970 | 27 | 36,926,033 | TT [5] |
| NS0092616 | 16 | 36,982,118 | GG [3] |
| NGMAX009107570 | 28 | 35,225,113 | AA [6] |
| NGMAX009108170 | 29 | 34,216,603 | TT [7] |
| NGMAX008369686 | 17 | 42,381,189 | GG |
| NGMAX008369687 | 18 | 42,381,227 | CC |
| NGMAX008369685 | 19 | 42,381,244 | AA |
| NGMAX008369688 | 20 | 42,381,285 | GG |
| NGMAX008369689 | 21 | 42,381,312 | AA |

[1] The relative positions of the 5' telomere proximal nucleotide of the listed markers or loci based on nucleotide positions on an updated physical map of soybean linkage group D1b (chromosome 2) of Table 4 are provided where nucleotide position 0 (zero) is telomere proximal and nucleotide position 42,379,943 is centromere proximal. Polymorphic nucleotide bases are designated in the sequence listing provided herewith according to the WIPO Standard ST.25 (1998), as follows: r = g or a (purine); y = t/u or c (pyrimidine); m = a or c; (amino); k = g or t/u (keto); s = g or c (strong interactions 3 H-bonds); w = a or t/u (weak interactions 2H-bonds); b = g or c or t/u (not a); d = a or g or t/u (not c); h = a or c or t/u (not g); v = a or g or c (not t, not u); and n = a or g or c or t/u (unknown, or other; any.)
[2] Both the maternal and paternal alleles of the single nucleotide polymorphisms that can be associated with a stem canker resistance phenotype are shown.
[3] The identified polymorphic allele of marker NS0092616 is/are located at nucleotide 293 of SEQ ID NO: 16.
[4] The identified polymorphic allele of marker NGMAX009107770 is/are located at nucleotide 101 of SEQ ID NO: 26.
[5] The identified polymorphic allele of marker NGMAX009107970 is/are located at nucleotide 101 of SEQ ID NO: 27.
[6] The identified polymorphic allele of marker NGMAX009107570 is/are located at nucleotide 101 of SEQ ID NO: 28.
[7] The identified polymorphic allele of marker NGMAX009108170 is/are located at nucleotide 101 of SEQ ID NO: 29.

Also provided herein are sub-regions of the linkage group D1b region that is flanked by loci NGMAX008369670 and NGMAX008369689 that are associated with a stem canker resistance phenotype. Sub-regions of the linkage group D1b region associated with a stem canker resistance phenotype include, but are not limited to sub-regions flanked by or including any of the following sets of loci: loci NGMAX008369675 and loci NGMAX008369689; loci NGMAX008369673 and loci NGMAX008369689; NGMAX008369676 and loci NGMAX008369689; loci NGMAX008369683 and loci NGMAX008369689; loci NGMAX008369675 and loci NGMAX008369686; loci NGMAX008369673 and loci NGMAX008369686; loci NGMAX008369676 and loci NGMAX008369686; or, loci NGMAX008369683 and loci NGMAX008369686. Sub-regions of the linkage group D1b region associated with a stem canker resistance phenotype also include, but are not limited to sub-regions flanked by a combination of: a) at least one telomere proximal marker selected from the group consisting of NGMAX008369670, NGMAX008369671, NGMAX008369675, NGMAX008369672, NGMAX008369673, NGMAX008369674, NGMAX008369676, NGMAX008369677, NGMAX008369680, NGMAX008369678, NGMAX008369679, NGMAX008369681, NGMAX008369682, NGMAX008369684, and NGMAX008369683; and; b) at least one centromere proximal marker selected from the group consisting of NGMAX008369686, NGMAX008369687, NGMAX008369685, NGMAX008369688, and NGMAX008369689.

These loci flank sub-regions that spans telomere proximal nucleotide 19007046 to centromere proximal nucleotide 42379943 in the physical map of linkage group D1b provided in Tables 3 and 4. Polymorphisms located in this first sub-region that are associated with a stem canker resistance phenotype can be detected with markers that include, but are not limited to, at least one marker selected from the group consisting of NGMAX009107570 (SEQ ID NO: 28), NGMAX009107770 (SEQ ID NO: 26), NGMAX009107970 (SEQ ID NO: 27), and NGMAX009108170 (SEQ ID NO: 29), and NS0092616 (SEQ ID NO: 16).

Additional genetic markers can be used either in conjunction with the markers provided in Table 1, 2, 3 and/or Table 4 or independently of the markers provided in Table 1, 2, 3, and/or Table 4 to practice the methods of the instant invention. Publicly available marker databases from which useful markers can be obtained include, but are not limited to, the soybase.org website on the interne (World Wide Web) that is administered by the United States Agricultural Research Service, the United States Department of Agriculture, and Iowa State University. Additional soybean markers that can be used and that have been described in the literature include, but are not limited to, Hyten et al., BMC Genomics. 11:38, 2010; Choi et al., Genetics. 176(1):685-96, 2007; Yoon et al., Theor Appl Genet. 2007 March; 114(5):885-99; and Hyten et al. Crop Sci. 2010 50: 960-968. Given the provision herein of a genomic region on linkage group D1b (chromosome 2) delimited or flanked by the including, but not limited to, telomere proximal loci NGMAX008369619, NGMAX008369622, NGMAX008369632, NGMAX008369642, NGMAX008369650, NGMAX008369658, NGMAX008369665, NGMAX008369669, or NGMAX008369668 of Table 3 or 4 and centromere proximal loci including, but not limited to, NGMAX008369690, NGMAX008369693, NGMAX008369691, NGMAX008369692, NGMAX008369694, NGMAX008369699, NGMAX008369695, NGMAX008369696, NGMAX008369697, or NGMAX008369698 of Table 3 or 4 as well as an assortment of soybean germplasms exhibiting either a stem canker susceptible or a stem canker resistance phenotype, additional markers located either within or near this genomic region that are associated with these phenotypes can be obtained by merely typing the new markers in the various germplasms provided herewith. The genomic region on linkage group D1b (chromosome 2) delimited or flanked by telomere proximal loci including, but not limited to, NGMAX008369619, NGMAX008369622, NGMAX008369632, NGMAX008369642, NGMAX008369650, NGMAX008369658, NGMAX008369665, NGMAX008369669, or NGMAX008369668 of Table 3 and 4 and centromere proximal loci including, but not limited to, NGMAX008369690, NGMAX008369693, NGMAX008369691, NGMAX008369692, NGMAX008369694, NGMAX008369699, NGMAX008369695, NGMAX008369696, NGMAX008369697, or NGMAX008369698 of Table 3 and 4 can also be mapped relative to markers provided in any publicly available or other soybean physical or genetic map to place this genetic locus on that map.

TABLE 3

Additional Markers in Linkage Group D1b

| Marker Annotation | LG | cM | Physical Map Start Nucleotide | Physical Map Stop Nucleotide | Annotation [1] |
|---|---|---|---|---|---|
| NGMAX008369619 | 2 | 0.1 | 182,825 | 186,960 | |
| NGMAX008369620 | 2 | 0.1 | 182,825 | 186,960 | |
| NGMAX008369621 | 2 | 1 | 314,452 | 315,296 | |
| NGMAX008369622 | 2 | 1.5 | 379,806 | 384,959 | Q43840 NADH dehydrogenase 0; Q8LAL7 NADH dehydrogenase 0; Q43840 NADH dehydrogenase 0; Q8LAL7 NADH dehydrogenase 0; Q43840 NADH dehydrogenase 0 |
| NGMAX008369623 | 2 | 3.4 | 634,489 | 639,070 | A4ZVI6 Phosphate transporter 0; Q9AVQ9 Phosphate transporter 0 |

TABLE 3-continued

Additional Markers in Linkage Group D1b

| Marker Annotation | LG | cM | Physical Map Start Nucleotide | Physical Map Stop Nucleotide | Annotation [1] |
|---|---|---|---|---|---|
| NGMAX008369624 | 2 | 3.4 | 634,489 | 639,070 | A4ZVI6 Phosphate transporter 0; Q9AVQ9 Phosphate transporter 0 |
| NGMAX008369625 | 2 | 3.4 | 634,489 | 639,070 | A4ZVI6 Phosphate transporter 0; Q9AVQ9 Phosphate transporter 0 |
| NGMAX008369627 | 2 | 4.9 | 822,824 | 829,169 | Q94IH6 CjMDR1 0 |
| NGMAX008369626 | 2 | 8.2 | 1,271,072 | 1,276,344 | P38661 Probable protein disulfide-isomerase A6 precursor 1E-176; Q9SXW4 Disulfide-isomerase 6E-11 |
| NGMAX008369628 | 2 | 8.4 | 1,299,612 | 1,300,297 | |
| NGMAX008369629 | 2 | 11.9 | 1,780,216 | 1,785,450 | |
| NGMAX008369630 | 2 | 13 | 1,937,286 | 1,938,896 | Q9M9S1 F14L17.20 protein 1E-159 |
| NGMAX008369631 | 2 | 14.4 | 2,122,367 | 2,129,798 | O04559 T7N9.16 1E-129 |
| NGMAX008369632 | 2 | 15.7 | 2,308,114 | 2,310,598 | Q7XA40 Putative disease resistance protein RGA3 1E-167; Q7XBQ9 Disease resistance protein RGA2 1E-163 |
| NGMAX008369635 | 2 | 17.7 | 2,422,613 | 2,425,521 | |
| NGMAX008369634 | 2 | 17.7 | 2,422,613 | 2,425,521 | |
| NGMAX008369633 | 2 | 18.2 | 2,584,729 | 2,585,192 | Q93Z89 Matrix metalloproteinase MMP2 7E-39; Q9ZR44 MtN9 protein 3E-17 |
| NGMAX008369636 | 2 | 18.8 | 2,882,332 | 2,894,207 | Q9LR91 T23E23.19 2E-68; Q84M95 At1g24030 1E-23; A7VM38 Receptor-like kinase 2E-21 |
| NGMAX008369637 | 2 | 18.8 | 2,882,332 | 2,894,207 | Q9LR91 T23E23.19 2E-68; Q84M95 At1g24030 1E-23; A7VM38 Receptor-like kinase 2E-21 |
| NGMAX008369638 | 2 | 18.8 | 2,882,332 | 2,894,207 | Q9LR91 T23E23.19 2E-68; Q84M95 At1g24030 1E-23; A7VM38 Receptor-like kinase 2E-21 |
| NGMAX008369639 | 2 | 24.5 | 3,424,200 | 3,428,928 | Q93X76 Putative carboxyl-terminal proteinase 0 |
| NGMAX008369641 | 2 | 26.5 | 3,600,433 | 3,600,743 | Q3LVN8 TO43-3rc 7E-13; Q9ZSA8 F3H7.16 protein (Putative Fe(II)/ascorbate oxidase) 4E-12 |
| NGMAX008369640 | 2 | 28 | 3,751,554 | 3,752,869 | Q9ZRX9 Cyclin D2.1 protein 1E-35; Q5XLI2 D-type cyclin 4E-35 |
| NGMAX008369642 | 2 | 28 | 3,751,554 | 3,752,869 | Q9ZRX9 Cyclin D2.1 protein 1E-35; Q5XLI2 D-type cyclin 4E-35 |
| NGMAX008369643 | 2 | 31 | 4,048,458 | 4,053,450 | |
| NGMAX008369644 | 2 | 42.2 | 5,647,399 | 5,651,984 | Q6RYA0 Salicylic acid-binding protein 2 1E-75 |
| NGMAX008369645 | 2 | 46.4 | 6,203,958 | 6,205,944 | A2Q5Q2 Zinc finger, GATA-type 9E-66 |

TABLE 3-continued

Additional Markers in Linkage Group D1b

| Marker Annotation | LG | cM | Physical Map Start Nucleotide | Physical Map Stop Nucleotide | Annotation [1] |
|---|---|---|---|---|---|
| NGMAX008369646 | 2 | 57.7 | 7,570,040 | 7,574,605 | Q53D73 Fe-superoxide dismutase 1 1E-130; Q8W596 Fe-superoxide dismutase 1E-125 |
| NGMAX008369647 | 2 | 57.9 | 7,718,575 | 7,719,385 | |
| NGMAX008369648 | 2 | 57.9 | 7,718,575 | 7,719,385 | |
| NGMAX008369653 | 2 | 58.2 | 8,040,465 | 8,044,355 | |
| NGMAX008369649 | 2 | 58.4 | 8,123,595 | 8,125,219 | |
| NGMAX008369650 | 2 | 58.7 | 8,245,113 | 8,267,316 | A2Q5X7 Ovarian tumour, otubain, putative 6E-49; A2Q3G4 Ovarian tumour, otubain 2E-39 |
| NGMAX008369652 | 2 | 59.8 | 8,712,285 | 8,712,518 | |
| NGMAX008369651 | 2 | 59.8 | 8,712,285 | 8,712,518 | |
| NGMAX008369654 | 2 | 60.5 | 9,014,120 | 9,018,553 | |
| NGMAX008369655 | 2 | 60.5 | 9,014,120 | 9,018,553 | |
| NGMAX008369656 | 2 | 60.5 | 9,014,120 | 9,018,553 | |
| NGMAX008369657 | 2 | 60.5 | 9,014,120 | 9,018,553 | |
| NGMAX008369659 | 2 | 60.5 | 9,014,120 | 9,018,553 | |
| NGMAX008369658 | 2 | 61 | 9,218,816 | 9,220,704 | Q45EZ4 RAV-like DNA-binding protein 1E-127 |
| NGMAX008369660 | 2 | 61.3 | 9,344,254 | 9,350,049 | Q6NQK2 At1g25580 1E-125 |
| NGMAX008369662 | 2 | 62.7 | 9,708,089 | 9,716,695 | |
| NGMAX008369661 | 2 | 62.7 | 9,708,089 | 9,716,695 | |
| NGMAX008369664 | 2 | 63.1 | 9,816,145 | 9,817,884 | Q8W3P8 ABA-glucosyltransferase 0 |
| NGMAX008369663 | 2 | 63.5 | 9,908,775 | 9,910,264 | |
| NGMAX008369666 | 2 | 64.9 | 10,064,476 | 10,064,926 | Q5EAE9 RING-H2 finger protein ATL5C precursor 1E-28 |
| NGMAX008369667 | 2 | 82.6 | 14,111,955 | 14,112,212 | |
| NGMAX008369665 | 2 | 94.4 | 15,082,151 | 15,083,827 | Q05929 EDGP precursor 1E-166 |
| NGMAX008369669 | 2 | 96.4 | 15,269,035 | 15,271,944 | |
| NGMAX008369668 | 2 | 96.5 | 15,278,399 | 15,281,648 | Q9ZVT8 F15K9.3 1E-114 |
| NGMAX008369670 | 2 | 100 | 19,007,046 | 19,008,654 | O23637 Argininosuccinate lyase 2E-25; A3ZRX1 Argininosuccinate lyase 1E-9 |
| NGMAX008369671 | 2 | 100.6 | 21,409,115 | 21,411,764 | Q9C536 Copia-type polyprotein, putative 1E-87; Q9M197 Copia-type reverse transcriptase-like protein 3E-85 |
| NGMAX008369675 | 2 | 101 | 23,428,066 | 23,432,753 | |
| NGMAX008369672 | 2 | 101.8 | 27,316,222 | 27,325,497 | |
| NGMAX008369673 | 2 | 102.1 | 28,450,255 | 28,450,720 | Q8GXV7 Cysteine-rich repeat secretory protein 56 precursor 2E-21 |
| NGMAX008369674 | 2 | 103.1 | 32,813,596 | 32,814,765 | Q9FRR2 F22O13.25 6E-12 |
| NGMAX008369676 | 2 | 103.1 | 32,982,299 | 32,985,399 | Q9FG27 Similarity to transfactor 3E-52 |
| NGMAX008369677 | 2 | 103.2 | 33,592,314 | 33,592,973 | |
| NGMAX008369680 | 2 | 103.4 | 34,212,327 | 34,219,634 | |
| NGMAX008369678 | 2 | 103.4 | 34,255,783 | 34,256,523 | |
| NGMAX008369679 | 2 | 103.4 | 34,297,519 | 34,299,678 | A2Q3L3 Apple; Protein kinase; EGF-like, subtype 2; Curculin-like (Mannose-binding) lectin 1E-166; Q7XSF1 OSJNBb0066J23.17 protein 1E-59 |

TABLE 3-continued

Additional Markers in Linkage Group D1b

| Marker Annotation | LG | cM | Physical Map Start Nucleotide | Physical Map Stop Nucleotide | Annotation [1] |
|---|---|---|---|---|---|
| NGMAX008369681 | 2 | 103.4 | 34,297,519 | 34,299,678 | A2Q3L3 Apple; Protein kinase; EGF-like, subtype 2; Curculin-like (Mannose- binding) lectin 1E-166; Q7XSF1 OSJNBb0066J23.17 protein 1E-59 |
| NGMAX008369682 | 2 | 103.5 | 35,077,968 | 35,080,920 | O22938 Putative receptor-like protein kinase 1E-116 |
| NGMAX008369684 | 2 | 103.6 | 35,163,509 | 35,163,914 | |
| NGMAX008369683 | 2 | 103.6 | 36,290,051 | 36,302,843 | Q66MH7 MAPKK 1E-158 |
| NS0092616 | 2 | 107 | | | |
| NGMAX009107570 | 2 | 107.10 | 35,225,113 | 35,225,313 | Putative Glucosyltransferase |
| NGMAX008369687 | 2 | 110.5 | 42,379,943 | 42,381,801 | |
| NGMAX008369685 | 2 | 110.5 | 42,379,943 | 42,381,801 | |
| NGMAX008369688 | 2 | 110.5 | 42,379,943 | 42,381,801 | |
| NGMAX008369689 | 2 | 110.5 | 42,379,943 | 42,381,801 | |
| NGMAX008369690 | 2 | 120.6 | 44,042,891 | 44,044,510 | |
| NGMAX008369693 | 2 | 121.7 | 44,108,787 | 44,109,479 | |
| NGMAX008369691 | 2 | 125.4 | 44,292,431 | 44,293,959 | O82019 Polygalacturonase precursor 6E-91; Q40312 Polygalacturonase precursor 2E-87 |
| NGMAX008369692 | 2 | 125.4 | 44,292,431 | 44,293,959 | O82019 Polygalacturonase precursor 6E-91; Q40312 Polygalacturonase precursor 2E-87 |
| NGMAX008369694 | 2 | 128.8 | 44,864,155 | 44,866,185 | Q9FH50 APO protein 3, mitochondrial precursor 1E-132 |
| NGMAX008369699 | 2 | 155 | 47,727,254 | 47,729,887 | O22889 Putative PTR2 family peptide transporter 0 |
| NGMAX008369695 | 2 | 176.5 | 50,263,019 | 50,267,472 | Q9LT41 RCD1 1E-133 |
| NGMAX008369696 | 2 | 176.7 | 50,286,646 | 50,289,952 | Q43086 Aspartate carbamoyltransferase 1, chloroplast precursor 1E-173; Q43064 Aspartate carbamoyltransferase 3, chloroplast precursor 1E-154 |
| NGMAX008369697 | 2 | 177.1 | 50,336,001 | 50,343,043 | |
| NGMAX008369698 | 2 | 177.5 | 50,379,681 | 50,385,665 | Q8S9L5 Peptidyl-prolyl cis-trans isomerase 0 |

[1] Annotation provided shows related genes showing some identity to the marker or locus and/or the identity of a gene at the marker locus.

Sequences for genes provided above can be obtained from either the listing of sequences provided herewith in the Summary Table of Nucleic Acid Sequences in the Examples (Table 13) and/or the Sequence Listing, or on the World Wide Web (or Internet) using the identifiers provided in Column 1 (Locus/Display Name) from the following interne locations:

a) "soybase.org" (described in Grant et al., Nucleic Acids Research, 2010, Vol. 38, Database issue D843-D846) or soybase.org/gbrowse/cgi-bin/gbrowse/gmax1.01/(see Hyten D L, Choi I-Y, Song Q, Specht J E, Carter T E et al. (2010) A high density integrated genetic linkage map of soybean and the development of a 1,536 Universal Soy Linkage Panel for QTL mapping. *Crop Science* 50:960-968 and Hyten D L, Cannon S B, Song Q, Weeks N, Fickus E W et al. (2010). High-throughput SNP discovery through deep resequencing of a reduced representation library to anchor and orient scaffolds in the soybean whole genome sequence. *BMC Genomics* 11(1): 38).

b) "phytozome.net" or "phytozome.net/cgi-bin/gbrowse/soybean/?name=Gm09";

c) "www.plantgdb.org" or "plantgdb.org/GmGDB/ (Assembly version Glyrnal.170 (April 2009)"; and, d) "ncbi.nlm.nih.gov/sites/entrez" and subsites "ncbi.nlm.nih.gov/nucest", "ncbi.nlm.nih.gov/dbEST", "ncbi.nlm.nih.gov/genbank/", ".ncbi.nlm.nih.gov/sites/genome", "ncbi.nlm.nih.gov/unigene", and "ncbi.nlm.nih.gov/UniGene/UGOrg.cgi?TAXID=3847".

TABLE 4

Additional Markers in Updated Physical Map of Linkage Group D1b

| Marker Annotation | LG | cM | Updated Physical Map Start Nucleotide | Updated Physical Map Stop Nucleotide | Annotation [1] |
|---|---|---|---|---|---|
| NGMAX008369668 | 2 | 99.49 | 15,279,358 | 15,279,558 | Q9ZVT8 F15K9.3 1E-114 |
| NGMAX008369670 | 2 | 104.72 | 19,096,714 | 19,096,914 | O23637 Argininosuccinate lyase 2E-25; A3ZRX1 Argininosuccinate lyase 1E-9 |
| NGMAX008369671 | 2 | 104.58 | 21,422,629 | 21,422,829 | Q9C536 Copia-type polyprotein, putative 1E-87; Q9M197 Copia-type reverse transcriptase-like protein 3E-85 |
| NGMAX008369675 | 2 | 105.74 | 23,739,140 | 23,739,340 | |
| NGMAX008369672 | 2 | 106.95 | 27,331,328 | 27,331,528 | |
| NGMAX008369673 | 2 | 107.26 | 28,463,620 | 28,463,820 | Q8GXV7 Cysteine-rich repeat secretory protein 56 precursor 2E-21 |
| NGMAX008369674 | 2 | 108.34 | 32,862,267 | 32,862,467 | Q9FRR2 F22O13.25 6E-12 |
| NGMAX008369676 | 2 | 108.38 | 33,024,826 | 33,025,026 | Q9FG27 Similarity to transfactor 3E-52 |
| NGMAX008369677 | 2 | 108.54 | 33,608,159 | 33,608,359 | |
| NGMAX008369680 | 2 | 108.73 | 34,235,541 | 34,235,741 | |
| NGMAX008369678 | 2 | 108.73 | 34,262,903 | 34,263,103 | |
| NGMAX008369679 | 2 | 108.76 | 34,308,875 | 34,309,075 | A2Q3L3 Apple; Protein kinase; EGF-like, subtype 2; Curculin-like (Mannose-binding) lectin 1E-166; Q7XSF1 OSJNBb0066J23.17 protein 1E-59 |
| NGMAX008369681 | 2 | 108.76 | 34,308,895 | 34,309,095 | A2Q3L3 Apple; Protein kinase; EGF-like, subtype 2; Curculin-like (Mannose-binding) lectin 1E-166; Q7XSF1 OSJNBb0066J23.17 protein 1E-59 |
| NGMAX008369682 | 2 | 108.96 | 35,080,156 | 35,080,356 | O22938 Putative receptor-like protein kinase 1E-116 |
| NGMAX008369684 | 2 | 108.99 | 35,201,653 | 35,201,853 | |
| N6MAX008369683 | 2 | 109.25 | 36,311,905 | 36,312,105 | Q66MH7 MAPKK 1E-158 |
| NGMAX009107770 | 2 | 105.67 | 37,347,910 | 37,348,110 | Glycosyl hydrolase family 3 C terminal domain |

TABLE 4-continued

Additional Markers in Updated Physical Map of Linkage Group D1b

| Marker Annotation | LG | cM | Updated Physical Map Start Nucleotide | Updated Physical Map Stop Nucleotide | Annotation [1] |
|---|---|---|---|---|---|
| NGMAX009107970 | 2 | 105.83 | 36,926,033 | 36,926,233 | AP2 domain: transcription factor activity; Ethylene mediated signaling pathway |
| NS0092616 | 2 | 108.80 | 36,982,118 | 36,982,630 | |
| NGMAX009107570 | 2 | 107.12 | 35,225,113 | 35,225,313 | Putative Glucosyltransferase |
| NGMAX009108170 | 2 | 107.9 | 34,216,603 | 34,216,772 | Antiporter Activity/ Multidrug transport |
| NGMAX008369686 | 2 | 115.58 | 42,381,189 | 42,381,389 | |
| NGMAX008369687 | 2 | 115.58 | 42,381,227 | 42,381,427 | |
| NGMAX008369685 | 2 | 115.58 | 42,381,244 | 42,381,444 | |
| NGMAX008369688 | 2 | 115.58 | 42,381,285 | 42,381,485 | |
| NGMAX008369689 | 2 | 115.58 | 42,381,312 | 42,381,512 | |
| NGMAX008369690 | 2 | 127.61 | 44,050,509 | 44,050,709 | |

[1] Annotation provided shows related genes showing some identity to the marker or locus and/or the identity of a gene at the marker locus.

Sequences for genes provided above can be obtained from either the listing of sequences provided herewith in the Summary Table of Nucleic Acid Sequences in the Examples (Table 12) and/or the Sequence Listing, or on the World Wide Web (or Internet) using the identifiers provided in Column 1 (Locus/Display Name) from the following interne locations:

a) "soybase.org" (described in Grant et al., Nucleic Acids Research, 2010, Vol. 38, Database issue D843-D846) or soybase.org/gbrowse/cgi-bin/gbrowse/gmax1.01/(see Hyten D L, Choi I-Y, Song Q, Specht J E, Carter T E et al. (2010) A high density integrated genetic linkage map of soybean and the development of a 1,536 Universal Soy Linkage Panel for QTL mapping. *Crop Science* 50:960-968 and Hyten D L, Cannon S B, Song Q, Weeks N, Fickus E W et al. (2010). High-throughput SNP discovery through deep resequencing of a reduced representation library to anchor and orient scaffolds in the soybean whole genome sequence. *BMC Genomics* 11(1): 38).

b) "phytozome.net" or "phytozome.net/cgi-bin/gbrowse/soybean/?name=Gm09";

c) "www.plantgdb.org" or "plantgdb.org/GmGDB/ (Assembly version Glyrnal.170 (April 2009)"; and, d) "ncbi.nlm.nih.gov/sites/entrez" and subsites "ncbi.nlm.nih.gov/nucest", "ncbi.nlm.nih.gov/dbEST", "ncbi.nlm.nih.gov/genbank/", ".ncbi.nlm.nih.gov/sites/genome", "ncbi.nlm.nih.gov/unigene", and "ncbi.nlm.nih.gov/UniGene/UGOrg.cgi?TAXID=3847".

IV. Identification of Plants Exhibiting the Stem Canker Resistant Phenotype

To observe the presence or absence of the stem canker resistance phenotypes, soybean plants comprising genotypes of interest can be exposed to stem cankers in seedling stages, early to mid-vegetative growth stages, or in early reproductive stages. The design and execution of stem canker exposure experiments to assess tolerance have been described in numerous publications including, but not limited to, Pioli et al. *Phytopathology* 93:136-146, 2330; and Keeling, *Plant Disease* 72:217-220, 1988. In certain embodiments, the hypocotyls of seedlings or the stems of plants can be inoculated with *Diaporthe* by insertion of toothpicks or other devices comprising the fungi. Resistance can be determined by exposing the plants to stem cankers and measuring any plant growth feature that is impacted by stem canker infestation. In certain embodiments, resistance can be assessed by measuring a soybean yield parameter. Soybean yield parameters that can be examined to assess stem canker tolerance include, but are not limited to, average seed weight, average seeds per pod, average number of pods per plant, chlorophyll content.

A rating scale that evaluates the degree of stem canker resistance can also be employed to identify "stem canker susceptible" and "stem canker resistance" plants. An exemplary and non limiting scale for evaluating the stem canker susceptibility phenotype is as follows, where the low numbers correspond to an "stem canker resistance" phenotype and the high numbers correlate to an "stem canker susceptible" phenotype.

An exemplary rating and damage system that can be used in stem inoculation or other assays is a Percentage of Dead Plants Rating is as described in Table 5.

TABLE 5

Description of an exemplary rating scale used for stem canker resistance phenotyping

| Rating | Percentage of Dead Plants (% DP) |
|---|---|
| R = Resistant | 0-25% DP |
| MR = Moderately resistant | 26-50% DP |
| MS = Moderately susceptible | 51-75% DP |
| S = Susceptible | 76-90% DP |
| HS = Highly susceptible | Above 90% DP |

The percentage of dead plants can be calculated using the formula:

Percentage of Dead Plants or % DP Score (Per Pot):

$$\frac{\text{\# of Dead Plants} + (\text{\# of Infected Plants}/2)}{\text{Total Number of Plants}} \times 100$$

In certain embodiments, the plants can be assigned a damage index (DI), which is calculated using the following formula:

$$DI = \frac{\sum (\text{Each scale} \times \text{Number of plants in the scale})}{4 \times \text{Total number of plants evaluated}} \times 100$$

In this formula, a higher damage index corresponds to a more susceptible plant.

In other embodiments, a 0-5 scale essentially similar to that described by Keeling in *Plant Disease* 72:217-220, 1988 can be used. In brief, stems are inoculated by insertion of a toothpick or other device, the plants are permitted to grow for a sufficient period of time for disease to be manifest (about 30 to about 50 days in typical growing conditions), the stems are split and the distance of disease progression from the site of inoculation to the base of the stem is measured. This distance is converted to a disease rating value as follows: 0=no lesions, 1=1 mm or less, 2=1.1 to 3 mm, 3=3.1 to 6 mm, 4=6.1 to 10 mm, 5=10 mm or more. Plants with the highest scores are the least resistant such that plants scoring a "5" have chlorotic stems and are dying.

V. Introgression of a Genomic Region Associated with a Stem Canker Resistance Phenotype Also provided herewith are unique soybean germplasms comprising an introgressed genomic region that is associated with a stem canker resistance phenotype and methods of obtaining the same. Marker-assisted introgression involves the transfer of a chromosomal region, defined by one or more markers, from one germplasm to a second germplasm. Offspring of a cross that contain the introgressed genomic region can be identified by the combination of markers characteristic of the desired introgressed genomic region from a first germplasm (i.e. such as a stem canker resistance germplasm) and both linked and unlinked markers characteristic of the desired genetic background of a second germplasm (i.e. a stem canker susceptible germplasm). In addition to the markers provided herewith that identify alleles of genomic region that is associated with a stem canker resistance phenotype, flanking markers that fall on both the telomere proximal end of the genomic region on linkage group D1b (chromosome 2) and the centromere proximal end of the linkage group D1b (chromosome 2) genomic region are also provided in Tables 1, 3, 4, and 6. Such flanking markers are useful in a variety of breeding efforts that include, but are not limited to, introgression of the genomic region associated with a stem canker resistance phenotype into a genetic background comprising markers associated with germplasm that ordinarily contains the allelic forms of the genomic region that is associated with a "stem canker susceptible" phenotype. Numerous markers that are linked and either immediately adjacent or adjacent to a linkage group D1b stem canker resistance QTL in soybean that permit introgression of the stem canker resistance QTL in the absence of extraneous linked DNA from the source germplasm containing the QTL are provided herewith. In certain embodiments, the linked and immediately adjacent markers are within about 105 kilobases (kB), 80 kB, 60 kB, 50 kB, 40 kB, 30 kB, 20 kB, 10 kB, 5 kB, 1 kB, 0.5 kB, 0.2 kB, or 0.1 kB of the introgressed genomic region. In certain embodiments, the linked and adjacent markers are within 1,000 kB, 600 kB, 500 kB, 400 kB, 300 kB, 200 kB, 150 kB of the introgressed genomic region. In certain embodiments, genomic regions comprising some or all of a stem canker resistance QTL on linkage group D1b (chromosome 2) that are delimited by the following markers of Table 6 can be introgressed into the genomes of susceptible varieties by using markers that include, but are not limited to, adjacent markers and/or immediately adjacent markers provided in Tables 1, 3, 4, or 6. Those skilled in the art will appreciate that when seeking to introgress a smaller genomic region comprising a stem canker resistance locus of Table 6 that any of the telomere proximal or centromere proximal markers that are immediately adjacent to a larger genomic region comprising a stem canker resistance locus can also be used to introgress that smaller genomic region.

TABLE 6

Genomic Regions containing Stem canker Resistance Loci, Exemplary Adjacent Markers, and Exemplary Immediately Adjacent Markers for Introgression

| Genomic Region Comprising a linkage group D1b Stem canker Resistance Locus | Immediately Adjacent Telomere Proximal Markers [1] | Immediately Adjacent Centromere Proximal Markers [2] |
|---|---|---|
| a) loci NGMAX008369670 and NGMAX008369689 | NGMAX008369665 NGMAX008369669 NGMAX008369668 | NGMAX008369690 NGMAX008369693 NGMAX008369691 NGMAX008369692 |
| b) loci NGMAX008369675 and loci NGMAX008369689 | NGMAX008369670 NGMAX008369671 | NGMAX008369690 NGMAX008369693 NGMAX008369691 NGMAX008369692 |
| c) loci NGMAX008369673 and loci NGMAX008369689 | NGMAX008369675 NGMAX008369672 | NGMAX008369690 NGMAX008369693 NGMAX008369691 NGMAX008369692 |
| d) loci NGMAX008369676 and loci NGMAX008369689 | NGMAX008369673 NGMAX008369674 | NGMAX008369690 NGMAX008369693 NGMAX008369691 NGMAX008369692 |
| e) loci NGMAX008369683 and loci NGMAX008369689 | NGMAX008369677 NGMAX008369680 NGMAX008369678 NGMAX008369679 NGMAX008369681 NGMAX008369682 NGMAX008369684 | NGMAX008369690 NGMAX008369693 NGMAX008369691 NGMAX008369692 |
| f) loci NGMAX008369675 and loci NGMAX008369686 | NGMAX008369670 NGMAX008369671 | NGMAX008369687 NGMAX008369685 NGMAX008369688 NGMAX008369689 |
| g) loci NGMAX008369673 and loci NGMAX008369686 | NGMAX008369675 NGMAX008369672 | NGMAX008369687 NGMAX008369685 NGMAX008369688 NGMAX008369689 |
| h) loci NGMAX008369676 and loci NGMAX008369686 | NGMAX008369673 NGMAX008369674 | NGMAX008369687 NGMAX008369685 NGMAX008369688 NGMAX008369689 |
| i) loci NGMAX008369683 and loci NGMAX008369686 | NGMAX008369677 NGMAX008369680 NGMAX008369678 NGMAX008369679 NGMAX008369681 NGMAX008369682 NGMAX008369684 | NGMAX008369687 NGMAX008369685 NGMAX008369688 NGMAX008369689 |

[1] Closely associated markers located between the telomere and the genomic region containing a stem canker resistance locus.
[2] Closely associated markers located between the centromere and the genomic region containing a stem canker resistance locus.

Provided herein are methods of introgressing any of the genomic regions comprising a linkage group D1b stem canker resistance locus of Table 6 into soybean germplasm that lacks such a linkage group D1b stem canker resistance locus. In certain embodiments, the soybean germplasm that lacks such a genomic region comprising linkage group D1b stem canker resistance locus is stem canker susceptible or has less than optimal levels of stem canker resistance. In certain embodiments, the methods of introgression provided herein can yield soybean plants comprising introgressed genomic regions comprising a linkage group D1b stem canker resistance locus of Table 6 where the immediately adjacent genomic DNA and/or some or all of the adjacent genomic DNA between the introgressed genomic region and the telomere or centromere will comprise allelic forms of the markers of Tables, 1, 3, 4, or 6 that are characteristic of the germplasm into which the genomic region is introgressed and distinct from the germplasm from which the genomic region is derived. In certain embodiments, the soybean germplasm into which the genomic region is introgressed is germplasm that lacks such a linkage group D1b stem canker resistance locus. In certain embodiments, the soybean germplasm into which the genomic region is introgressed is germplasm that lacks such a linkage group D1b stem canker resistance locus and is either stem canker susceptible or has less than optimal levels of stem canker resistance. In certain embodiments, the germplasm from which the linkage group D1b stem canker resistance locus is obtained comprises D85-10404, D85-10412, soybean variety AG6730, or Dowling germplasm or germplasm derived from D85-10404, D85-10412, soybean variety AG6730, or Dowling germplasm.

Also provided herein are soybean plants produced by the aforementioned methods of introgression. In certain embodiments, such soybean plants will comprising introgressed genomic regions comprising a linkage group D1b stem canker resistance locus of Table 6 where the immediately adjacent genomic DNA and/or some or all of the adjacent genomic DNA between the introgressed genomic region and the telomere or centromere will comprise allelic forms of the markers of Tables 1, 3, 4, or 6 that are characteristic of the germplasm into which the genomic region is introgressed and distinct from the germplasm from which the genomic region is derived. In an exemplary embodiment where a genomic region flanked by, or including, markers NGMAX008369670 and NGMAX008369689 is introgressed, plants comprising that linkage group D1b genomic region containing a stem canker resistance locus wherein one or more of the adjacent or immediately adjacent telomere proximal markers of Table 3, Table 4, or Table 6 and one or more of the adjacent centromere or immediately adjacent centromere proximal markers of Table 3 and Table 6, can comprise allelic forms that are characteristic of the germplasm into which the genomic region is introgressed and/or that are distinct from the germplasm from which the genomic region is derived. In an exemplary embodiment where a genomic region flanked by or including markers NGMAX008369670 and NGMAX008369689 is introgressed, plants comprising that linkage group D1b genomic region containing a stem canker resistance locus wherein one or more of the adjacent or immediately adjacent telomere proximal markers NGMAX008369619, NGMAX008369622, NGMAX008369632, NGMAX008369642, NGMAX008369650, NGMAX008369658, NGMAX008369665, NGMAX008369669, and NGMAX008369668, and one or more of the adjacent or immediately adjacent centromere proximal markers NGMAX008369690, NGMAX008369693, NGMAX008369691, NGMAX008369692, NGMAX008369694, NGMAX008369699, NGMAX008369695, NGMAX008369696, NGMAX008369697, and/or NGMAX008369698, can comprise allelic forms that are characteristic of the germ plasm into which the genomic region is introgressed and/or that are distinct from the germplasm from which the genomic region is derived. In another exemplary embodiment where a genomic region flanked by, or including, markers NGMAX008369683 and NGMAX008369686 is introgressed, plants comprising that linkage group D1b genomic region containing a stem canker resistance locus wherein one or more of the adjacent or immediately adjacent telomere proximal markers of Table 3, 4, and Table 6 and one or more of the adjacent centromere or immediately adjacent centromere proximal markers of Table 3, Table 4, and Table 6 can comprise allelic forms that are characteristic of the germ plasm into which the genomic region is introgressed and/or that are distinct from the germplasm from which the genomic region is derived. In another exemplary embodiment where a genomic region flanked by, or including, markers NGMAX008369683 and NGMAX008369686 is introgressed, plants comprising that linkage group D1b genomic region containing a stem canker resistance locus wherein one or more of the adjacent or immediately adjacent telomere proximal markers NGMAX008369619, NGMAX008369622, NGMAX008369632, NGMAX008369642, NGMAX008369650, NGMAX008369658, NGMAX008369665, NGMAX008369669, NGMAX008369668, NGMAX008369670, NGMAX008369671, NGMAX008369675, NGMAX008369672, NGMAX008369673, NGMAX008369674, NGMAX008369677, NGMAX008369680, NGMAX008369678, NGMAX008369679, NGMAX008369681, NGMAX008369682, and/or NGMAX008369684, and wherein one or more of the adjacent or immediately adjacent centromere proximal markers NGMAX008369687, NGMAX008369685, NGMAX008369688, NGMAX008369689, NGMAX008369690, NGMAX008369693, NGMAX008369691, NGMAX008369692, NGMAX008369694, NGMAX008369699, NGMAX008369695, NGMAX008369696, NGMAX008369697, and/or NGMAX008369698, can comprise allelic forms that are characteristic of the germ plasm into which the genomic region is introgressed and/or that are distinct from the germplasm from which the genomic region is derived.

Additional markers located on linkage group D1b (chromosome 2) and other chromosomes useful for introgressing a linkage group D1b soybean stem canker resistance QTL are disclosed in US Patent Publication 20090049565. Publicly available marker databases from which additional useful markers located on linkage group D1b (chromosome 2) and other chromosomes can be obtained include, but are not limited to, the soybase.org website on the interne that is administered by the United States Agricultural Research Service, the United States Department of Agriculture, and Iowa State University. Soybean plants or germplasm comprising an introgressed genomic region that is associated with a stem canker resistance phenotype wherein at least 10%, 25%, 50%, 75%, 90%, or 99% of the remaining genomic sequences carry markers characteristic of soybean plants or germplasm that are otherwise or ordinarily comprise a genomic region associated with the stem canker susceptible phenotype are thus provided. Furthermore soybean plants comprising an introgressed region where closely linked regions adjacent and/or immediately adjacent to the linkage group D1b regions provided herewith that comprise genomic sequences carrying markers characteristic of soybean plants or germplasm that are otherwise or ordinarily comprise a genomic region associated with the stem canker susceptible phenotype are also provided.

Soybean Plants Comprising a Genomic Region Associated with a Stem Canker Resistance Phenotype Also provided herein are soybean plants comprising linkage group D1b genomic regions associated with a stem canker resistance phenotype wherein immediately adjacent genomic regions and/or one or more adjacent genomic regions characteristic of soybean germplasms that lack the genomic regions associated with a stem canker resistance phenotype and/or that are distinct from the germplasm from which the genomic region is derived. In certain embodiments, such plants can be produced by the aforementioned methods of introgression. In certain embodiments, soybean plants comprising a linkage group D1b stem canker resistance locus of Table 6 where the immediately adjacent genomic DNA and/or some or all of the adjacent genomic DNA between the introgressed genomic region and the telomere or centromere will comprise allelic forms of the markers of Tables 1, 2, 3, 4, or 6 that are characteristic of germplasms that lack the linkage group D1b genomic regions of Table 6 comprising a stem canker resistance phenotype and/or that are distinct from the germplasm from which the genomic region is derived.

Also provided herein are soybean plants comprising genomic regions containing the stem canker resistance loci. In certain embodiments, such soybean plants will comprise introgressed genomic regions comprising a linkage group D1b stem canker resistance locus of Table 6 where the immediately adjacent genomic DNA and/or some or all of the adjacent genomic DNA between the introgressed genomic region and the telomere or centromere will comprise allelic forms of the markers of Tables 1, 3, 4, or 6 that are characteristic of the germ plasm into which the genomic region is introgressed and distinct from the germplasm from which the genomic region is derived. In an exemplary embodiment where a genomic region flanked by, or including, markers NGMAX008369670 and NGMAX008369689 is introgressed, plants comprising that linkage group D1b genomic region containing a stem canker resistance locus wherein one or more of the adjacent or immediately adjacent telomere proximal markers of Tables 3, 4 and Table 6 and one or more of the adjacent centromere or immediately adjacent centromere proximal markers of Tables 3, 4, and Table 6, can comprise allelic forms that are characteristic of the germ plasm into which the genomic region is introgressed and/or that are distinct from the germplasm from which the genomic region is derived. In an exemplary embodiment where a genomic region flanked by or including markers NGMAX008369670 and NGMAX008369689 is introgressed, plants comprising that linkage group D1b genomic region containing a stem canker resistance locus wherein one or more of the adjacent or immediately adjacent telomere proximal markers NGMAX008369619, NGMAX008369622, NGMAX008369632, NGMAX008369642, NGMAX008369650, NGMAX008369658, NGMAX008369665, NGMAX008369669, and NGMAX008369668, and one or more of the adjacent or immediately adjacent centromere proximal markers NGMAX008369690, NGMAX008369693, NGMAX008369691, NGMAX008369692, NGMAX008369694, NGMAX008369699, NGMAX008369695, NGMAX008369696, NGMAX008369697, and/or NGMAX008369698, can comprise allelic forms that are characteristic of the germ plasm into which the genomic region is introgressed and/or that are distinct from the germplasm from which the genomic region is derived. In another exemplary embodiment where a genomic region flanked by, or including, markers NGMAX008369683 and NGMAX008369686 is introgressed, plants comprising that linkage group D1b genomic region containing a stem canker resistance locus wherein one or more of the adjacent or immediately adjacent telomere proximal markers of Tables 3, 4, and Table 6 and one or more of the adjacent centromere or immediately adjacent centromere proximal markers of Tables 3, 4, and Table 6, can comprise allelic forms that are characteristic of the germ plasm into which the genomic region is introgressed and/or that are distinct from the germplasm from which the genomic region is derived. In another exemplary embodiment where a genomic region flanked by, or including, markers NGMAX008369683 and NGMAX008369686 is introgressed, plants comprising that linkage group D1b genomic region containing a stem canker resistance locus wherein one or more of the adjacent or immediately adjacent telomere proximal markers NGMAX008369619, NGMAX008369622, NGMAX008369632, NGMAX008369642, NGMAX008369650, NGMAX008369658, NGMAX008369665, NGMAX008369669, NGMAX008369668, NGMAX008369670, NGMAX008369671, NGMAX008369675, NGMAX008369672, NGMAX008369673, NGMAX008369674, NGMAX008369677, NGMAX008369680, NGMAX008369678, NGMAX008369679, NGMAX008369681, NGMAX008369682, and/or NGMAX008369684, and wherein one or more of the adjacent or immediately adjacent centromere proximal markers NGMAX008369687, NGMAX008369685, NGMAX008369688, NGMAX008369689, NGMAX008369690, NGMAX008369693, NGMAX008369691, NGMAX008369692, NGMAX008369694, NGMAX008369699, NGMAX008369695, NGMAX008369696, NGMAX008369697, and/or NGMAX008369698, can comprise allelic forms that are characteristic of the germ plasm into which the genomic region is introgressed and/or that are distinct from the germplasm from which the genomic region is derived.

As used herein, a maturity group refers to an industry division of groups of varieties based range in latitude which the plant is best adapted and most productive. Soybean varieties are classified into 13 recognized maturity groups with the designations ranging from maturity groups 000, 00, 0, and I through X, wherein 000 represents the earliest maturing variety and X represents the latest maturing variety. Soybean plants in maturity groups 000 to IV have indeterminate plant habit, while soybean plants in maturity groups V through X have determinate plant habit. Herein, determinate growth habit refers to a cease vegetative growth after the main stem terminates in a cluster of mature pods. Herein, indeterminate growth habit refers to the development of leaves and flowers simultaneously throughout a portion of their reproductive period, with one to three pods at the terminal apex. Early maturity varieties (000 to IV) are adapted to northern latitudes with longer day lengths with the maturity designation increasing in southern latitudes with shorter day lengths.

Herein, relative maturity refers to a soybean plant maturity group subdividing a maturity group into tenths, for example III.5. Relative maturity provided a more exact maturity. The number following the decimal point refers to the relative earliness or lateness with a maturity group, examples of which including IV.2 is an early group IV variety and IV.9 is a late group IV.

It is further understood that a soybean plant of the present invention may exhibit the characteristics of any relative maturity group. In an aspect, the relative maturity group is selected from the group consisting of 000.1-000.9, 00.1-00.9, 0.1-0.9, I.1-I.9, II.1-II.9, III.1-III.9, IV.1-IV.9, V.1-V.9, VI.1-VI.9, VII.1-VII.9, VIII.1-VIII.9, IX.1-IX.9, and X.1-X.9. The pollen for selected soybean plant can be cryopreserved and used in crosses with soybean lines from other maturity groups to introgress a stem canker resistance locus in a line that would not normally be available for crossing in nature. Pollen cryopreservation techniques are well known in the art (Tyagi and Hymowitz, *Cryo letters* 24: 119-124 (2003), Liang et al. *Acta Botanica Sinica* 35: 733-738 (1993)).

VI. Soybean Donor Plants Comprising Genomic Region Associated with the Stem Canker Resistance Phenotypes A stem canker resistant QTL allele or alleles can be introduced from any plant that contains that allele (donor) to any recipient soybean plant. In one aspect, the recipient soybean plant can contain additional stem canker resistant loci. In another aspect, the recipient soybean plant can contain a transgene. In another aspect, while maintaining the introduced QTL, the genetic contribution of the plant providing the stem canker resistant QTL can be reduced by back-crossing or other suitable approaches. In one aspect, the nuclear genetic material derived from the donor material in the soybean plant can be less than or about 50%, less than or about 25%, less than or about 13%, less than or about 5%, 3%, 2% or 1%, but that genetic material contains the stem canker resistant locus or loci of interest Plants containing one or more stem canker resistant loci described can be donor plants. Stem canker plants containing resistant loci can be, examples of which including screened for by using a nucleic acid molecule capable of detecting a marker polymorphism associated with resistance. Soybean donor plants comprising a genomic region containing a linkage group D1b stem canker resistance locus include, but are not limited to, D85-10404, D85-10412, soybean variety AG6730, Dowling, and derivatives thereof. In certain embodiments, a donor plant can be a susceptible line. In certain embodiments, a donor plant can also be a recipient soybean plant Also provided herewith are additional soybean plants that comprising a genomic region associated with a stem canker resistance phenotype that are identified by use of the markers provided in Tables 1, 2, 3, 4, and/or Table 6 and/or methods provided herein. Any of the soybean plants identified herein or other soybean plants that are otherwise identified using the markers or methods provided herein can be used in methods that include, but are not limited to, methods of obtaining soybean plants with an introgressed stem canker resistance locus, obtaining a soybean plant that exhibits a stem canker resistance phenotype, or obtaining a soybean plant comprising in its genome a genetic region associated with a stem canker resistance phenotype.

In certain embodiments, the soybean plants provided herein or used in the methods provided herein can comprise a transgene that confers tolerance to glyphosate. Transgenes that can confer tolerance to glyphosate include, but are not limited to, transgenes that encode glyphosate tolerant Class I EPSPS (5-enolpyruvylshikimate-3-phosphate synthases) enzymes or glyphosate tolerant Class II EPSPS (5-enolpyruvylshikimate-3-phosphate synthases) enzymes. Useful glyphosate tolerant EPSPS enzymes provided herein are disclosed in U.S. Pat. No. 6,803,501, RE39,247, U.S. Pat. No. 6,225,114, U.S. Pat. No. 5,188,642, and U.S. Pat. No. 4,971,908. In certain embodiments, the glyphosate tolerant soybean plants can comprise a transgene encoding a glyphosate oxidoreductase or other enzyme which degrades glyphosate. Glyphosate oxidoreductase enzymes had been described in U.S. Pat. No. 5,776,760 and U.S. Reissue Pat. RE38,825. In certain embodiments the soybean plant can comprise a transgene encoding a glyphosate N-acetyltransferase gene that confers tolerance to glyphosate. In certain embodiments, the soybean plant can comprise a glyphosate n-acetyltransferase encoding transgene such as those described in U.S. Pat. No. 7,666,644. In still other embodiments, soybean plants comprising combinations of transgenes that confer glyphosate tolerance are provided. Soybean plants comprising both a glyphosate resistant EPSPS and a glyphosate N-acetyltransferase are also provided herewith. In certain embodiments, it is contemplated that the soybean plants used herein can comprise one or more specific genomic insertion(s) of a glyphosate tolerant transgene including, but not limited to, as those found in: i) MON89788 soybean (deposited under ATCC accession number PTA-6708 and described in US Patent Application Publication Number 20100099859), ii) GTS 40-3-2 soybean (Padgette et al., Crop Sci. 35: 1451-1461, 1995), iii) event 3560.4.3.5 soybean (seed deposited under ATCC accession number PTA-8287 and described in US Patent Publication 20090036308), or any combination of i (MON89788 soybean), ii (GTS 40-3-2 soybean), and iii (event 3560.4.3.5 soybean).

An stem canker resistance QTL of the present invention may also be introduced into an soybean line comprising one or more transgenes that confer tolerance to herbicides including, but not limited to, glufosinate, dicamba, chlorsulfuron, and the like, increased yield, insect control, fungal disease resistance, virus resistance, nematode resistance, bacterial disease resistance, mycoplasma disease resistance, modified oils production, high oil production, high protein production, germination and seedling growth control, enhanced animal and human nutrition, low raffinose, environmental stress resistant, increased digestibility, industrial enzymes, pharmaceutical proteins, peptides and small molecules, improved processing traits, improved flavor, nitrogen fixation, hybrid seed production, reduced allergenicity, biopolymers, and biofuels among others. These agronomic traits can be provided by the methods of plant biotechnology as transgenes in soybean.

In certain embodiments, it is contemplated that genotypic assays that provide for non-destructive identification of the plant or plants can be performed either in seed, the emergence stage, the "VC" stage (i.e. cotyledons unfolded), the V1 stage (appearance of first node and unifoliate leaves), the V2 stage (appearance of the first trifoliate leaf), and thereafter. In certain embodiments, non-destructive genotypic assays are performed in seed using apparati and associated methods as described in U.S. Pat. Nos. 6,959,617; 7,134,351; 7,454,989; 7,502,113; 7,591,101; 7,611,842; and 7,685,768, which are incorporated herein by reference in their entireties. In certain embodiments, non-destructive genotypic assays are performed in seed using apparati and associated methods as described in US Patent Application Publications 20100086963, 20090215060, and 20090025288, which are incorporated herein by reference in their entireties. Published U.S. Patent Applications US 2006/0042527, US 2006/0046244, US 2006/0046264, US 2006/0048247, US 2006/0048248, US 2007/0204366, and US 2007/0207485, which are incorporated herein by reference in their entirety, also disclose apparatus and systems for the automated sampling of seeds as well as methods of sampling, testing and bulking seeds. Thus, in a certain embodiments, any of the methods provided herein can comprise screening for markers in individual seeds of a population wherein only seed with at least one genotype of interest is advanced.

VII. Molecular Assisted Breeding Techniques

Genetic markers that can be used in the practice of the instant invention include, but are not limited to, are Restriction Fragment Length Polymorphisms (RFLP), Amplified Fragment Length Polymorphisms (AFLP), Simple Sequence Repeats (SSR), Single Nucleotide Polymorphisms (SNP), Insertion/Deletion Polymorphisms (Indels), Variable Number Tandem Repeats (VNTR), and Random Amplified Polymorphic DNA (RAPD), and others known to those skilled in the art. Marker discovery and development in crops provides the initial framework for applications to marker-assisted breeding activities (US Patent Applications 2005/0204780, 2005/0216545, 2005/0218305, and 2006/00504538). The resulting "genetic map" is the representation of the relative position of characterized loci (DNA markers or any other locus for which alleles can be identified) along the chromosomes. The measure of distance on this map is relative to the frequency of crossover events between sister chromatids at meiosis.

As a set, polymorphic markers serve as a useful tool for fingerprinting plants to inform the degree of identity of lines or varieties (U.S. Pat. No. 6,207,367). These markers can form a basis for determining associations with phenotype and can be used to drive genetic gain. The implementation of marker-assisted selection is dependent on the ability to detect underlying genetic differences between individuals.

Certain genetic markers for use in the present invention include "dominant" or "codominant" markers. "Codominant markers" reveal the presence of two or more alleles (two per diploid individual). "Dominant markers" reveal the presence of only a single allele. The presence of the dominant marker phenotype (e.g., a band of DNA) is an indication that one allele is present in either the homozygous or heterozygous condition. The absence of the dominant marker phenotype (e.g., absence of a DNA band) is merely evidence that "some other" undefined allele is present. In the case of populations where individuals are predominantly homozygous and loci are predominantly dimorphic, dominant and codominant markers can be equally valuable. As populations become more heterozygous and multiallelic, codominant markers often become more informative of the genotype than dominant markers.

In another embodiment, markers that include. but are not limited, to single sequence repeat markers (SSR), AFLP markers, RFLP markers, RAPD markers, phenotypic markers, isozyme markers, single nucleotide polymorphisms (SNPs), insertions or deletions (Indels), single feature polymorphisms (SFPs, for example, as described in Borevitz et al. 2003 Gen. Res. 13:513-523), microarray transcription profiles, DNA-derived sequences, and RNA-derived sequences that are genetically linked to or correlated with stem canker resistance loci, regions flanking stem canker resistance loci, regions linked to stem canker resistance loci, and/or regions that are unlinked to stem canker resistance loci can be used in certain embodiments of the instant invention.

In one embodiment, nucleic acid-based analyses for determining the presence or absence of the genetic polymorphism (i.e. for genotyping) can be used for the selection of seeds in a breeding population. A wide variety of genetic markers for the analysis of genetic polymorphisms are available and known to those of skill in the art. The analysis may be used to select for genes, portions of genes, QTL, alleles, or genomic regions (Genotypes) that comprise or are linked to a genetic marker that is linked to or correlated with stem canker resistance loci, regions flanking stem canker resistance loci, regions linked to stem canker resistance loci, and/or regions that are unlinked to stem canker resistance loci can be used in certain embodiments of the instant invention.

Herein, nucleic acid analysis methods include, but are not limited to, PCR-based detection methods (for example, TaqMan assays), microarray methods, mass spectrometry-based methods and/or nucleic acid sequencing methods. In one embodiment, the detection of polymorphic sites in a sample of DNA, RNA, or cDNA may be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis, fluorescence detection methods, or other means.

A method of achieving such amplification employs the polymerase chain reaction (PCR) (Mullis et al. 1986 Cold Spring Harbor Symp. Quant. Biol. 51:263-273; European Patent 50,424; European Patent 84,796; European Patent 258,017; European Patent 237,362; European Patent 201,184; U.S. Pat. No. 4,683,202; U.S. Pat. No. 4,582,788; and U.S. Pat. No. 4,683,194), using primer pairs that are capable of hybridizing to the proximal sequences that define a polymorphism in its double-stranded form.

Methods for typing DNA based on mass spectrometry can also be used. Such methods are disclosed in U.S. Pat. Nos. 6,613,509 and 6,503,710, and references found therein.

Polymorphisms in DNA sequences can be detected or typed by a variety of effective methods well known in the art including, but not limited to, those disclosed in U.S. Pat. Nos. 5,468,613, 5,217,863; 5,210,015; 5,876,930; 6,030,787; 6,004,744; 6,013,431; 5,595,890; 5,762,876; 5,945,283; 5,468,613; 6,090,558; 5,800,944; 5,616,464; 7,312,039; 7,238,476; 7,297,485; 7,282,355; 7,270,981 and 7,250,252 all of which are incorporated herein by reference in their entireties. However, the compositions and methods of the present invention can be used in conjunction with any polymorphism typing method to type polymorphisms in genomic DNA samples. These genomic DNA samples used include but are not limited to genomic DNA isolated directly from a plant, cloned genomic DNA, or amplified genomic DNA.

For instance, polymorphisms in DNA sequences can be detected by hybridization to allele-specific oligonucleotide (ASO) probes as disclosed in U.S. Pat. Nos. 5,468,613 and 5,217,863. U.S. Pat. No. 5,468,613 discloses allele specific oligonucleotide hybridizations where single or multiple nucleotide variations in nucleic acid sequence can be detected in nucleic acids by a process in which the sequence containing the nucleotide variation is amplified, spotted on a membrane and treated with a labeled sequence-specific oligonucleotide probe.

Target nucleic acid sequence can also be detected by probe ligation methods as disclosed in U.S. Pat. No. 5,800,944 where sequence of interest is amplified and hybridized to probes followed by ligation to detect a labeled part of the probe.

Microarrays can also be used for polymorphism detection, wherein oligonucleotide probe sets are assembled in an overlapping fashion to represent a single sequence such that a difference in the target sequence at one point would result in partial probe hybridization (Borevitz et al., Genome Res. 13:513-523 (2003); Cui et al., Bioinformatics 21:3852-3858 (2005). On any one microarray, it is expected there will be a plurality of target sequences, which may represent genes and/or noncoding regions wherein each target sequence is represented by a series of overlapping oligonucleotides, rather than by a single probe. This platform provides for high throughput screening a plurality of polymorphisms. A single-feature polymorphism (SFP) is a polymorphism detected by a single probe in an oligonucleotide array, wherein a feature is a probe in the array. Typing of target sequences by microarray-based methods is disclosed in U.S. Pat. Nos. 6,799,122; 6,913,879; and 6,996,476.

Target nucleic acid sequence can also be detected by probe linking methods as disclosed in U.S. Pat. No. 5,616,464, employing at least one pair of probes having sequences homologous to adjacent portions of the target nucleic acid sequence and having side chains which non-covalently bind to form a stem upon base pairing of the probes to the target nucleic acid sequence. At least one of the side chains has a photoactivatable group which can form a covalent cross-link with the other side chain member of the stem.

Other methods for detecting SNPs and Indels include single base extension (SBE) methods. Examples of SBE methods include, but are not limited, to those disclosed in U.S. Pat. Nos. 6,004,744; 6,013,431; 5,595,890; 5,762,876; and 5,945,283. SBE methods are based on extension of a nucleotide primer that is adjacent to a polymorphism to incorporate a detectable nucleotide residue upon extension of the primer. In certain embodiments, the SBE method uses three synthetic oligonucleotides. Two of the oligonucleotides serve as PCR primers and are complementary to sequence of the locus of genomic DNA which flanks a region containing the polymorphism to be assayed. Following amplification of the region of the genome containing the polymorphism, the PCR product is mixed with the third oligonucleotide (called an extension primer) which is designed to hybridize to the amplified DNA adjacent to the polymorphism in the presence of DNA polymerase and two differentially labeled dideoxynucleosidetriphosphates. If the polymorphism is present on the template, one of the labeled dideoxynucleosidetriphosphates can be added to the primer in a single base chain extension. The allele present is then inferred by determining which of the two differential labels was added to the extension primer. Homozygous samples will result in only one of the two labeled bases being incorporated and thus only one of the two labels will be detected. Heterozygous samples have both alleles present, and will thus direct incorporation of both labels (into different molecules of the extension primer) and thus both labels will be detected.

In another method for detecting polymorphisms, SNPs and Indels can be detected by methods disclosed in U.S. Pat. Nos. 5,210,015; 5,876,930; and 6,030,787 in which an oligonucleotide probe having a 5' fluorescent reporter dye and a 3' quencher dye covalently linked to the 5' and 3' ends of the probe. When the probe is intact, the proximity of the reporter dye to the quencher dye results in the suppression of the reporter dye fluorescence, e.g. by Forster-type energy transfer. During PCR forward and reverse primers hybridize to a specific sequence of the target DNA flanking a polymorphism while the hybridization probe hybridizes to polymorphism-containing sequence within the amplified PCR product. In the subsequent PCR cycle DNA polymerase with 5'→3' exonuclease activity cleaves the probe and separates the reporter dye from the quencher dye resulting in increased fluorescence of the reporter.

In another embodiment, the locus or loci of interest can be directly sequenced using nucleic acid sequencing technologies. Methods for nucleic acid sequencing are known in the art and include technologies provided by 454 Life Sciences (Branford, Conn.), Agencourt Bioscience (Beverly, Mass.), Applied Biosystems (Foster City, Calif.), LI-COR Biosciences (Lincoln, Nebr.), NimbleGen Systems (Madison, Wis.), Illumina (San Diego, Calif.), and VisiGen Biotechnologies (Houston, Tex.). Such nucleic acid sequencing technologies comprise formats such as parallel bead arrays, sequencing by ligation, capillary electrophoresis, electronic microchips, "biochips," microarrays, parallel microchips, and single-molecule arrays, as reviewed by R.F. Service Science 2006 311:1544-1546.

The markers to be used in the methods of the present invention should preferably be diagnostic of origin in order for inferences to be made about subsequent populations. Experience to date suggests that SNP markers may be ideal for mapping because the likelihood that a particular SNP allele is derived from independent origins in the extant populations of a particular species is very low. As such, SNP markers appear to be useful for tracking and assisting introgression of QTLs, particularly in the case of genotypes.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Mapping Stem Canker Resistance

To map a QTL for stem canker resistance, three mapping populations were developed. The populations were as follows: D85-10412 (Population 1)×J77-339 F2:3, D85-10412×J77-339 F2:3 (Population 2), and Dowling×J77-339 F2:3. Fifteen plants (15) from 91 F2:3 families were screened using a toothpick method for evaluation of a stem canker resistance phenotype. These 12 to 15-day old plants were inoculated by inserting a *Diaporthe*-infested toothpick through the stem.

Plants were rated 21-24 days after inoculation by determining percent mortality in each F3 family. This was calculated using the formula:

Percentage of Dead Plants or % DP Score (Per Pot):

$$\frac{\# \text{ of Dead Plants} + (\# \text{ of Infected Plants}/2)}{\text{Total Number of Plants}} \times 100$$

The five categories were:

| | |
|---|---|
| R = Resistant | 0-25%DP |
| MR = Moderately resistant | 26-50% DP |
| MS = Moderately susceptible | 51-75% DP |
| S = Susceptible | 76-90% DP |
| HS = Highly susceptible | Above 90% DP |

The parents and progeny of each mapping population showed differing stem canker reactions (Table 7). Dowling was less resistant than D85-10412, and may be heterogeneous for stem canker resistance.

TABLE 7

Percentage of dead plants (% DP) from stem canker disease in the parents and progeny of three mapping populations.

| Population | Parent 1 (% DP) | Parent 2 (% DP) | Range of Progeny (% DP) | Mean of Progeny (% DP) |
|---|---|---|---|---|
| D85-10412 × J77-339 $F_{2:3}$ (Population 1) | 33 | 67 | 10-100 | 56 |
| D85-10412 × J77-339 $F_{2:3}$ (Population 2) | 10 | 78 | 0-96 | 26 |
| Dowling × J77-339 $F_{2:3}$ | 40 | 53 | 10-97 | 44 |

A trifoliolate leaflet was taken from each plant at inoculation, and all of the leaflets from each family were combined as a bulk for DNA extraction. The parents were fingerprinted with approximately 1500 SNP markers to find DNA marker polymorphisms. Both Dowling and D85-10412 (Population 1) have a QTL in a similar position on LG-D1b (Table 8) and NS0092616 is most significantly associated with the stem canker resistance trait.

TABLE 8

Map position, interval, and significance of alleles mapped in the D85-10404 and Dowling populations.

| Population | Linkage group | Interval | P-value | $R^2$ value |
|---|---|---|---|---|
| D85-10404 × J77-339 $F_{2:3}$ | D1b | 76-89 cM | $<10^{-5}$ | 45 |
| Dowling × J77-339 $F_{2:3}$ | D1b | 67-124 cM | 0.008 | 12 |

The stem canker resistance QTL maps to a similar interval in both populations, but the $R^2$ is higher in D85-10404 than in Dowling.

Example 2

Stem Canker Greenhouse Screening

Soybean plants were inoculated 12-15 days after planting by inserting a toothpick infested with *Diaporthe phaseolorum* f. sp. *meridionalis* (DPM) through the stem, approximately 0.5-1" below the cotyledon leaves (ends of toothpick should just protrude out the sides of the stem). Inoculate 15 plants per pot. Immediately, after inoculating up to two pots, place pots back in the humid tent (humid tent is created by covering the plants with plastic and turning on the misting system). High humidity conditions (>85%) after inoculation are necessary to accelerate the infection process. When inoculations are completed, mister is set for conditions to provide >85% relative humidity inside humid tent. Soybean plants are rated between 21 and 24 days after inoculation, or when known susceptible checks visually show symptoms associated with susceptibility (dead, dying plants). The number of plants inoculated, number of dead plants, and the number of infected, severely infected, and resistant plants are determined by splitting the stems. Classifications are determined based on: (1) Resistant: Plants that do not show any browning along the inside of the stem, only a small browning around the toothpick wound. (2) Infected: Plants that show browning inside the stem around the toothpick area that extends somewhat along the stem. (3) Severely infected plants: These plants show a solid browning inside the stem that covers most of the stem, the outside of the stem looks dried out around the toothpick wound and progresses along the stem, a sign that the plant will eventually die. A severely infected plant is considered a dead plant.

The percentage of dead plants can be calculated using the formula:

Percentage of Dead Plants or % DP Score (Per Pot):

$$\frac{\text{\# of Dead Plants} + (\text{\# of Infected Plants}/2)}{\text{Total Number of Plants}} \times 100$$

A phenotypic rating is assessed based on this result (Table 9).

TABLE 9

Phenotypic rating scale for Stem Canker Disease

| Rating | Percentage of Dead Plants (% DP) |
|---|---|
| R = Resistant | 0-25% DP |
| MR = Moderately resistant | 26-50% DP |
| MS = Moderately susceptible | 51-75% DP |
| S = Susceptible | 76-90% DP |
| HS = Highly susceptible | Above 90% DP |

Example 3

Fine Mapping Stem Canker Resistance

Fine mapping provides the greatest ability to compartmentalize variation responsible for soybean phenotypic traits of interest, especially those associated with disease resistance. The ability to identify the causative mutation, a tight disease resistance haplotype window, or a <1 kB linked marker provides the ability for robust deployment of marker assisted selection (MAS) or phenotypic prediction.

The methodology for fine mapping stem canker resistance is described in published patent application WO/2011/090987 and is incorporated herein by reference in its entirety. To fine map stem canker resistance, a D85-10412× J77-339 $F_{2:3}$ mapping population was phenotyped using the methodology in Example 2 and recombinant pools were generated.

At this point, sequence capture technology constructs a capture tiling path of 48,000 unique elements of the genome across all chromosomes onto a high definition Nimblegen array (Roche) that evenly covers the genome of the target soybean plant. The homozygous negative pool is then hybridized and the target tiling path for enriched. The homozygous positive pool is then hybridized and the tiling path enriched.

The two genomic libraries are both enriched for a certain fraction of the genome that is evenly spaced across each chromosome. These two libraries are then sequenced and mapped back to the soybean genome. SNPs are called within both the positive and negative libraries and the frequency of the SNPs is calculated within each library. In the ideal scenario, one part of the genome stands out as having a set of SNPs that are fixed between the two libraries while SNPs within the libraries are heterozygous. This is diagnostic of a region of the genome that is responsible for the phenotype of interest.

In the D85-10412×J77-339 $F_{2:3}$ fine mapping population experiments there was an increase in the linkage assessment score (LAS) on linkage group D1b between 33 Mb and 40 Mb. The LAS identifies potential SNPs with the greatest linkage to the stem canker resistance trait. of interest, and SNPs with the highest scores should have the closest linkage to the stem canker resistance trait. As a result, 4 of the highest eSNP LAS scores (from a total of 8 eSNPs) were selected for further analysis and conversion to TaqMan assay for validation. The four SNP markers selected and validated are NGMAX009107570 (SEQ ID NO: 28), NGMAX009107770 (SEQ ID NO: 26), NGMAX009107970 (SEQ ID NO: 27), and NGMAX009108170 (SEQ ID NO: 29).

Example 4

Exemplary Marker Assays for Detecting Polymorphisms

In one embodiment, the detection of polymorphic sites in a sample of DNA, RNA, or cDNA may be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis, fluorescence detection methods, or other means. Exemplary primers and probes for amplifying and detecting genomic regions associated with a dicamba tolerance phenotype are given in Table 12.

TABLE 10

Exemplary Assays for Detecting Polymorphisms

| Marker or Locus Name | Marker SEQ ID | SNP Position | SEQ ID NO Forward Primer | SEQ ID NO Reverse Primer | SEQ ID NO Probe 1 | SEQ ID NO Probe 2 |
|---|---|---|---|---|---|---|
| NS0092616 | 16 | 293 | 22 | 23 | 24 | 25 |
| NGMAX009107770 | 26 | 101 | 30 | 31 | 32 | 33 |
| NGMAX009107970 | 27 | 101 | 34 | 35 | 36 | 37 |
| NGMAX009107570 | 28 | 101 | 38 | 39 | 40 | 41 |
| NGMAX009108170 | 29 | 101 | 42 | 43 | 44 | 45 |

Example 5

Oligonucleotide Probes Useful for Detecting Polymorphisms by Single Base Extension Methods Oligonucleotides can also be used to detect or type the polymorphisms disclosed herein by single base extension (SBE)-based SNP detection methods. Exemplary oligonucleotides for use in SBE-based SNP detection are provided in Table 5. SBE methods are based on extension of a nucleotide primer that is hybridized to sequences adjacent to a polymorphism to incorporate a detectable nucleotide residue upon extension of the primer. It is also anticipated that the SBE method can use three synthetic oligonucleotides. Two of the oligonucleotides serve as PCR primers and are complementary to the sequence of the locus which flanks a region containing the polymorphism to be assayed. Exemplary PCR primers that can be used to type polymorphisms disclosed in this invention are provided in Table 4 in the columns labeled "Forward Primer SEQ ID" and "Reverse Primer SEQ ID". Following amplification of the region containing the polymorphism, the PCR product is hybridized with an extension primer which anneals to the amplified DNA adjacent to the polymorphism. DNA polymerase and two differentially labeled dideoxynucleoside triphosphates are then provided. If the polymorphism is present on the template, one of the labeled dideoxynucleoside triphosphates can be added to the primer in a single base chain extension. The allele present is then inferred by determining which of the two differential labels was added to the extension primer. Homozygous samples will result in only one of the two labeled bases being incorporated and thus only one of the two labels will be detected. Heterozygous samples have both alleles present, and will thus direct incorporation of both labels (into different molecules of the extension primer) and thus both labels will be detected. Exemplary forward and reverse SBE probes are provided in Table 13.

TABLE 11

Exemplary SBE Probes for Detecting Polymorphisms

| Marker or Locus Name | Marker (SEQ ID NO) | SNP Position | Probe (SBE) | Probe (SEQ ID NO) |
|---|---|---|---|---|
| NS0092616 | 16 | 293 | ACAAACAAAAAATC | 24 |
| NGMAX009107770 | 26 | 101 | CCCGTGGCAAGTAG | 32 |

TABLE 11-continued

Exemplary SBE Probes for Detecting Polymorphisms

| Marker or Locus Name | Marker (SEQ ID NO) | SNP Position | Probe (SBE) | Probe (SEQ ID NO) |
|---|---|---|---|---|
| NGMAX009107970 | 27 | 101 | CTGCTGCCTTTTCATC | 36 |
| NGMAX009107570 | 28 | 101 | CCATCTTCATACATGGACC | 40 |
| NGMAX009108170 | 29 | 101 | CTGAGCTTGCCTCCAAA | 44 |

Example 8

Summary Table of Nucleic Acid Sequences

TABLE 12

| Marker or Locus Name | SEQ ID NO: | Sequence |
|---|---|---|
| NGMAX008369670 | 1 | GCATCTTTCGGCCGAGACTGCAAAAA AGTCTCATTTGCTATCCGTCAGAATG AAAGTCTGGTAGCATGCAATGACGAA CGTCGTCATTTGCACCTTTCCTVGAG ATGTCAGCGTCTTCCGGTCGAGACTT TAAAAAAGTCTCATTTGCTATCCGTA AGACTCAAAGCCCGATAGTATGCATT GACTAACGATGTCATTTGC |
| NGMAX008369671 | 2 | AGCTTTGAAAGAACAAATGGCTTCTA TGATGGAGGCCATGCTAGGGATGAAA TGACTAATGGAGAGTAACGAGGCCAT CGCCGCCGCCGCTAGCATGGCTVTTG AGGCAGACCTGATTCTCCCGACTGCT GCACACCATCCTGTTCCAAACATTGT GGGACGAGGGAGAAGCACACCAGGGC ATGTCAGCAACCCCCATCT |
| NGMAX008369675 | 3 | TGCTGTCATTAGTGATTAAGAAAAGA GAAGAAAAGAGCTTTATAGTAACTCA TAACTTTGTAATCGTTTGGTTATAAA GATCTTTTCTTGGAAGTGAGTTVTGT CTTTTGAGTTGAAGAAGATCACCTCC TCAATCCAACAAGGTTTTTGTGGAAA TATTGGTGAGGTTGTATCTCTCTTGC TCGTTTTTTTTTGTGTAT |
| NGMAX008369672 | 4 | TGACTAATTGCTACTTATATATTAGT TAGTATACACCAGACAAATGGTCTAT TCCTGAACGAGAGTTAACATAGAGGA TTTAATAATGAAAGTAATTTGTVTAT TATTGATGGAATGGATCTAAATAAAG TAGGTGATTATTGGTAAAGTAATGA GTGGAGCCCACAAAATAGAAATGTAG CAGACAGAAAAATTAATGA |
| NGMAX008369673 | 5 | GCAAAACTAGGGTTTCTGTTTCTCTT TCCGAACTGAGTAGCAGCTCTGACCA TGGCAGAGGACCTTACTCATATATCGCT TAGTTGCTCGACCAAACCCTCCVCCC CGATGCCATTATCATTCGCACCGCCA CCGCCACCATCGTACTTAATCGTATC TCCCTCACTCTGCACTTCCCTTTCTA CCTCCTTTCCATTTCCACT |
| NGMAX008369674 | 6 | GGACACGGCCATACCCAATTTGGTTG CTCTTGAGGGGTTTCTTCGTGTATCA CAGCACCCATCCTTCGCACATCCAC GCCCCGCTGATAAAGCTTTGATHGAT GTGACATATGGGACTCCTTTCACTT GCAGCCTTTGCGGCTGGCCCGCGCTT CTCTCCCTCCTTTCTTGGGCAATCCT CCTTATGCCGGTGCGCGTA |
| NGMAX008369676 | 6 | GAACGTTGCGGTAGTCAAGTAGAAGA GCACTTCTCTAAACAAAGGCAAGGGA TAAACAACAAATGGCACAACATAGAC GGCGACAAAGCCGATGACAACGDCAG AGACAAAGGTTCCGGTGGAGAGAATG GCACCGAAGCCGATGCGGCATTGGTC GGCGCGGAGGGCAATGAGGGGGAAGA TGTCGAGGGTGCTGTTGCC |
| NGMAX008369677 | 8 | ATTTTCTCAAAGGTGTAAGCCTTTTG CGGAATCCACCTGCTAAGCGCTTCCC CACACACCGTTGTTAGCCAAGGTGGC CAGCCAGCTGCTACTTGCTCCCHCTA CAAATGCTTTGTTAGGTTTGATCTTC TTCGTTCACCCTTCGGTCGCCAAACC TGATCATCACCACCACCATTCTCTTC CTTCTCCTTCTCACCATTC |
| NGMAX008369680 | 9 | TATGATGATACAGGTCATGTGAGTAA GTGATATGTGTATAAGCATTTGATTG GGCTTGTTAATAAAATGTTATGTAAG ATTGATTCGGCCCTTCGTAACAHAAA AAAAATAATTGGGACAAAGGGTGACT AATAACAGTAAAAAACCTTATAGATT AGTCCTTAGGTAAAAAAAAATAGGGG TGTATTTAGTTACTATTTT |
| NGMAX008369678 | 10 | CTAGTCGGTAAAACCCCTCCTTTTTT ATGTACCACCCAACCATAATTGATGG CATACCACTAAACCATGGTTTTCACA TAACCGTTAACCTTAATAACACDCAT AACACTAAACCCTAAGTATTATACTA ACCCTAAACAGTTCGAACGTAAAGTA TAATACACAATTATATGAATTTCCAA CGTAAAGTATAGTACATGA |
| NGMAX008369679 | 11 | GACTATGTCATGTAACCTCCAACCTG CTTACTGGTGTATTGGCTTGCATAAG AGAGATAATCGTATAGGTACGCCTAT GCAGTGGCTCCCCAAGCGTACCAGTG GCAGTCATCCAGGTTGCTGGGGTAGA GGTAGGCAATGTGGACATGAGTCAAG GACTTATTAGGAAATATGTATTGTTG ACAAAGTGCAAAAGATAAC |
| NGMAX008369681 | 12 | AACCTGCTTACTGGTGTATTGGCTTG CATAAGAGAGATAATCGTATAGGTAC GCCTATGCAGTGGCTCCCCAAGCGTA CCGGTGGCAGTCATCCAGGTTGBTGG GGTAGAGGTAGGCAATGTGGACATGA GTCAAGGACTTATTAGGAAATATGTA TTGTTGACAAAGTGCAAAAGATAACC TATGGCAACTCACACGTAC |
| NGMAX008369682 | 13 | CCTTCTACATTATTGTTGCCAATTCG AACACTGTAAAGGGTTTGACAATTCC CAATTTCAACAGGAAGGTTACCACTT AAATTGTTCTGAGTGAGGATCABAAC ATTCTGCTTCCTAAAGTAAAAATGCT TCATGGTATAGGGCCTTCAAGGTTGT TTGAATGCAGATTAAGTATTTTAAGC TCAGAAATGAATCCAAGTG |
| NGMAX008369684 | 14 | TAATTTTGTGAAGAGAGGTTCTCAAT GGTAGAGTGATTTTAAGCAATTGTG AGATGTTTGATAATAGGTTGGGGTGG TTCCCAAAATGTATTGAGAGTGVTTG GTGAAGGTAGGGAAGTAAGCTTTTGC AACTCAAAGTGGGTTGGTAAGGAGAG CTTGGGCAAGAAATTTAATTGAATGT ACTTACATTTGGAACAAAA |
| NGMAX008369683 | 15 | AAAAGGGAAATTATAGGGTATTTAAA AGCCCTAAATCGCAAAGGAGCGTTT TCAGGTGACCTCGCCAACACCAATGG CGCCTTCACTTTCTGCAAAAAGHTGC TGCTACACGTAGGGGTAAAGCGCTGG TTTGACCAGCGACTCCACCCTGCATG GCCAAAGCGCCATTGCAGGTGGCGAT ACCAGTGCTGTCGCCAGTG |
| NS0092616 | 16 | AGCTTGCATGCCTGCAGAAAGATATG GAGCAATCAGATTAATTAAATTCAGT AAATGTAGGACCTCCAGGTGTTCATG TTTCAAAACCTTATCTTCTTTTACATT CATCAGAAGTGCTCAAAGCATTTAAT TTCAGTGCCAAAGCACTGCAACTTTT CAGCTCAGACAAAACAAACTTGCTAG CTTCCTTGGTAACTGTGGAGGATTTG ATAGACTTGAAAACCTTCTCAACAGA |

TABLE 12-continued

Nucleotide Sequences

| Marker or Locus Name | SEQ ID NO: | Sequence |
|---|---|---|
| | | TTCTTGAGCACATCTGCGTACCTAAA AAGCAAACAAACCACAACACAATTTA AACAAAVAAAAAATCCATAAGCTCAG AGTAATGAAATGATTAATAGGCATGG ACCAATGTCTCGAAATCAAAGGTCAT ATCATAACCAAATGCTGATTGCATTG TAAGGTAAAACCATCACCAAATCTAT ACATAATTGGATATAAACAAGGTTTA AAACTAAAGTTGCAGACACATTAGCA GCACCAAAAATTGCAGAATATTGAAA ATAGATTCAGTTGATTCCTTTTGAAA GTGA |
| NGMAX008369686 | 17 | CCATTATATGAATCAGAGTTTCAGAG AAAAGAGAACTTTTAGAAGAGAGACA TTTTAGTAAGAAGAGAGTATTATTGG ATTCAGTGTGTCTTAACATACA<u>V</u>ACT CATCCTCTTTATATAGGAGAGGATTC GAAACTAACATCCAAAATCTTATCCA TGAAAGGATAAAAGTGTCGTGCTAAT AACACAAAGGTCACGGGTT |
| NGMAX008369687 | 18 | TTAGAAGAGAGACATTTTAGTAAGAA GAGAGTATTATTGGATTCAGTGTGTC TTAACATACAGACTCATCCTCTTTAT ATAGGAGAGGATTCGAAACTAA<u>H</u>ATC CAAAATCTTATCCATGAAAGGATAAA AGTGTCGTGCTAATAACACAAAGGTC ACGGGTTTGAGACCTGCATGGGCCAA TCTATATGGGCTATACAG |
| NGMAX008369685 | 19 | TAGTAAGAAGAGAGTATTATTGGATT CAGTGTGTCTTAACATACAGACTCAT CCTCTTTATATAGGAGAGGATTCGAA ACTAACATCCAAAATCTTATCC<u>D</u>TGA AAGGATAAAAGTGTCGTGCTAATAAC ACAAAGGTCACGGGTTTGAGACCTGC ATGGGCCAATCTATATGGGCTATAC AGATTGTCAATCTGTATGG |
| NGMAX008369688 | 20 | TACAGACTCATCCTCTTTATATAGGA GAGGATTCGAAACTAACATCCAAAAT CTTATCCATGAAAGGATAAAAGTGTC GTGCTAATAACACAAAGGTCAC<u>DD</u>GG TTTGAGACCTGCATGGGCCAATCTAT ATGGGCTATACAGATTGTCAATCTG TATGGGCTATACGTAAGGACAATGTT GGAATTAATAAAAAGTTGAA |
| NGMAX008369689 | 21 | AGGATTCGAAACTAACATCCAAAATC TTATCCATGAAAGGATAAAAGTGTCG TGCTAATAACACAAAGGTCACGGGTT TGAGACCTGCATGGGCCAATCT<u>D</u>TAT GGGGCTATACAGATTGTCAATCTGTA TGGGCTATACGTAAGGACAATGTTGG AATTAATAAAAAGTTGAATGATGTAT ATGAGATTTGAATGGTGTA |
| NS0092616-F | 22 | AGCAAACAAACCACAACACAATTT |
| NS0092616-R | 23 | TCCATGCCTATTAATCATTTCATT ACTC |
| NS0092616-P1 | 24 | ACAAACAAAAAATC |
| NS0092616-P2 | 25 | AACAAAGAAAAAATC |

Polymorphic nucleotide bases are designated in Table 11 and in the sequence listing provided herewith according to the WIPO Standard ST.25 (1998), Table 1, as follows: r=g or a (purine); y=t/u or c (pyrimidine); m=a or c; (amino); k=g or t/u (keto); s=g or c (strong interactions 3H-bonds); w=a or t/u (weak interactions 2H-bonds); b=g or c or t/u (not a); d=a or g or t/u (not c); h=a or c or t/u (not g); v=a or g or c (not t, not u); and n=a or g or c or t/u (unknown, or other; any.)

Having illustrated and described the principles of the present invention, it should be apparent to persons skilled in the art that the invention can be modified in arrangement and detail without departing from such principles.

Although the materials and methods of this invention have been described in terms of various embodiments and illustrative examples, it will be apparent to those of skill in the art that variations can be applied to the materials and methods described herein without departing from the concept, spirit and scope of the invention. All such similar substitutes and modifications apparent to those skilled in the art are deemed to be within the spirit, scope and concept of the invention as defined by the appended claims.

What is claimed is:

1. A method of producing a population of soybean plants that comprises a genotype associated with a stem canker resistance phenotype, the method comprising:
   (i) genotyping a first population of soybean plants, wherein the first population contains at least one allele associated with the stem canker resistance phenotype, wherein the allele is located in at least one stem canker resistance marker locus, wherein the stem canker resistance marker locus is in a linkage group D1b genomic region, and wherein said genomic region is flanked by and including:
      a) loci NGMAX008369670 and NGMAX008369689;
      b) loci NGMAX008369675 and NGMAX008369689;
      c) loci NGMAX008369673 and NGMAX008369689;
      d) loci NGMAX008369676 and NGMAX008369689;
      e) loci NGMAX008369683 and NGMAX008369689;
      f) loci NGMAX008369675 and NGMAX008369686;
      g) loci NGMAX008369673 and NGMAX008369686;
      h) loci NGMAX008369676 and NGMAX008369686; or,
      i) loci NGMAX008369683 and NGMAX008369686,
   (ii) selecting from said first population of soybean plants based upon said genotyping one or more soybean plants comprising the at least one allele associated with a stem canker resistance phenotype; and
   (iii) producing offspring from the one or more selected soybean plants of the first population of soybean plants by crossing the selected soybean plant with another soybean plant,
   thereby producing a second population of soybean plants comprising a genotype associated with a stem canker resistant phenotype.

2. The method of claim 1, wherein said selected plant exhibits a stem canker resistance phenotype.

3. The method of claim 1, wherein said genotype associated with a stem canker resistance phenotype comprises at least one polymorphic allele of a marker flanked by and including loci NGMAX008369683 (SEQ ID NO: 15) and NGMAX008369686 (SEQ ID NO: 17).

4. The method of claim 1, wherein said genotype associated with a stem canker resistance phenotype comprises at least one polymorphic allele of at least one marker selected from the group consisting of NGMAX009107570 (SEQ ID NO: 28), NGMAX009107770 (SEQ ID NO: 26), NGMAX009107970 (SEQ ID NO: 27), and NGMAX009108170 (SEQ ID NO: 29), and NS0092616 (SEQ ID NO: 16).

* * * * *